US009689018B2

(12) United States Patent
Scholl et al.

(10) Patent No.: US 9,689,018 B2
(45) Date of Patent: *Jun. 27, 2017

(54) MIXED CELL DIAGNOSTIC SYSTEMS FOR DETECTION OF RESPIRATORY, HERPES AND ENTERIC VIRUSES

(71) Applicants: Diagnostic Hybrids Inc., Athens, OH (US); University Hospitals Cleveland Medical Center, Cleveland, OH (US)

(72) Inventors: David R. Scholl, Athens, OH (US); Yung T. Huang, Cleveland, OH (US); Patricia Gail Ray Goodrum, Athens, OH (US)

(73) Assignees: Diagnostic Hybrids, Inc., Athens, OH (US); University Hospitals Cleveland Medical Center, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/450,673

(22) Filed: Aug. 4, 2014

(65) Prior Publication Data

US 2015/0031016 A1    Jan. 29, 2015

Related U.S. Application Data

(60) Continuation of application No. 13/409,952, filed on Mar. 1, 2012, now Pat. No. 8,828,673, which is a continuation of application No. 12/253,127, filed on Oct. 16, 2008, now Pat. No. 8,142,997, which is a continuation of application No. 11/414,760, filed on Apr. 28, 2006, now Pat. No. 7,442,508, which is a continuation of application No. 11/231,552, filed on Sep. 20, 2005, now abandoned, which is a continuation-in-part of application No. 10/813,852, filed on Mar. 30, 2004, now Pat. No. 6,946,291, which is a continuation-in-part of application No. 10/407,789, filed on Apr. 4, 2003, now Pat. No. 6,875,600, which is a continuation of application No. 09/927,481, filed on Aug. 9, 2001, now Pat. No. 6,573,080, which is a continuation of application No. 09/661,849, filed on Sep. 14, 2000, now Pat. No. 6,376,172, which is a division of application No. 09/066,072, filed on Apr. 24, 1998, now Pat. No. 6,168,915.

(51) Int. Cl.
| | |
|---|---|
| *C12Q 1/02* | (2006.01) |
| *C12N 7/00* | (2006.01) |
| *C12Q 1/04* | (2006.01) |
| *C12Q 1/18* | (2006.01) |

(52) U.S. Cl.
CPC .............. *C12Q 1/02* (2013.01); *C12N 7/00* (2013.01); *C12Q 1/04* (2013.01); *C12Q 1/18* (2013.01); *C12N 2710/16611* (2013.01); *C12N 2760/16051* (2013.01); *C12N 2770/20011* (2013.01); *C12N 2770/32311* (2013.01); *G01N 2333/11* (2013.01); *G01N 2333/29* (2013.01); *G01N 2333/295* (2013.01)

(58) Field of Classification Search
CPC .............. A61K 2300/00; C07K 14/435; C12N 2502/025; C12N 2502/30; C12N 5/0605; C12N 2502/27; C12N 2503/00; C12N 2710/16651; C12N 2760/16251
See application file for complete search history.

(56) References Cited

U.S. PATENT DOCUMENTS

| | | | |
|---|---|---|---|
| 4,193,991 A | 3/1980 | Appel et al. ..................... 424/89 |
| 4,224,412 A | 9/1980 | Dorofeev et al. ............ 435/237 |
| 5,262,359 A | 11/1993 | Hierholzer ................. 435/235.1 |
| 5,418,132 A | 5/1995 | Olivo ............................... 435/5 |
| 5,891,624 A | 4/1999 | Huang ............................ 435/5 |
| 5,939,253 A | 8/1999 | Scholl et al. ..................... 435/5 |
| 5,958,676 A | 9/1999 | Olivo ............................... 435/5 |
| 6,071,744 A | 6/2000 | Scholl et al. ................. 435/325 |
| 6,071,774 A | 6/2000 | Sung et al. .................. 435/325 |
| 6,168,915 B1 | 1/2001 | Scholl et al. ..................... 435/5 |
| 6,306,582 B1 | 10/2001 | Scholl et al. ..................... 435/5 |
| 6,376,172 B1 * | 4/2002 | Scholl .................. C12N 5/0697 435/235.1 |
| 6,406,842 B2 * | 6/2002 | Scholl .................. C12N 5/0697 435/235.1 |
| 6,428,968 B1 | 8/2002 | Molnar-Kimber et al. . 435/7.23 |
| 6,573,080 B2 | 6/2003 | Scholl et al. .............. 435/235.1 |
| 6,875,600 B2 | 4/2005 | Scholl et al. .............. 435/235.1 |
| 6,946,291 B2 | 9/2005 | Scholl et al. ................. 435/325 |

(Continued)

FOREIGN PATENT DOCUMENTS

| | | |
|---|---|---|
| WO | WO 97/24461 | 7/1997 |
| WO | WO98/14469 | 4/1998 |

(Continued)

OTHER PUBLICATIONS

Ghahary et al. Journal of Cellular Physiology, 1999, vol. 180, pp. 61-70.*
Chan et al., "Human Metapneumovirus Detection in Patients with Severe Acute Respiratory Syndrome," *Emerging Infec. Dis.*, 9:1058-1063 (2003).
Frank et al., "Comparison of Different Tissue Cultures for Isolation and Quantitation of Influenza and Parainfluenza Viruses," *J. Clin. Microbiol.*, 10:32-36 (1979).
Rabalais et al., "Rapid Diagnosis of Respiratory Viral Infections by Using a Shell Vial Assay and Monoclonal Antibody Pool," *J. Clin. Microbiol.*, 30:1505-1508 (1992).

(Continued)

*Primary Examiner* — Bao Li
(74) *Attorney, Agent, or Firm* — Medlen & Carroll, LLP

(57) ABSTRACT

The present invention generally relates to the field of diagnostic microbiology, and, more particularly, to compositions and methods for detecting and differentiating one or more viruses or other intracellular parasites present in a specimen. The present invention also provides compositions and methods to evaluate the susceptibility of organisms to antimicrobial agents.

4 Claims, No Drawings

(56) References Cited

U.S. PATENT DOCUMENTS

| | | |
|---|---|---|
| 7,129,042 B2 | 10/2006 | Gillim-Ross et al. ............ 435/5 |
| 2003/0008816 A1 | 1/2003 | Pilon et al. ................ 424/185.1 |
| 2003/0215796 A1 | 11/2003 | Scholl et al. ...................... 435/5 |
| 2003/0232061 A1 | 12/2003 | Fouchier et al. ........... 424/211.1 |
| 2003/0232326 A1 | 12/2003 | Fouchier et al. ................... 435/5 |
| 2004/0005544 A1 | 1/2004 | Fouchier et al. ................. 435/5 |
| 2004/0005545 A1 | 1/2004 | Fouchier et al. ................. 435/5 |
| 2004/0170965 A1 | 9/2004 | Scholl et al. ...................... 435/5 |
| 2005/0256160 A1 | 11/2005 | Habashita et al. ............ 514/317 |
| 2006/0148830 A1 | 7/2006 | Terakado et al. .... A61K 31/517 |
| 2007/0037140 A1 | 2/2007 | Li et al. ............................ 435/5 |
| 2007/0042350 A1 | 2/2007 | Li et al. ............................ 435/5 |

FOREIGN PATENT DOCUMENTS

| | | |
|---|---|---|
| WO | WO 99/55917 | 4/1999 |
| WO | WO 02057302 A2 | 7/2002 |
| WO | WO 03072719 | 9/2003 |

OTHER PUBLICATIONS

Setterquist et al., "A Comparison of LLC-MK2 and R-MixTM (A549, MV1lu) Cells for the Detection of Human Metapneumovirus," 19th Annual Clinical Virology Symposium, Clearwater, FL, Apr. 27-30, 2003.

Smith et al., "Detection of Respiratory Syncytial virus in Nasopharyngeal Secretions by Shell Vial Technique," *J. Clin. Microbiol.*, 29:463-465 (1991).

Boshart et al., "A Very Strong Enhancer Is Located Upstream of an Immediate Early Gene of Human Cytomegalovirus," *Cell*, 41:521-530 (1985).

Dijkema et al., "Cloning and Expression of the Chromosomal Immune Interferon Gene of the Rat," *EMBO J.*, 4:761-767 (1985).

Gorman et al., "The Rous Sarcoma Virus Long Terminal Repeat is a Strong Promoter When Introduced into a Variety of Eukaryotic Cells by DNA-mediated Transfection," *Proc. Natl. Acad. Sci. USA*, 79:6777-6781 (1982).

Kim et al., "Use of the human elongation factor 1á promoter as a versatile and efficient expression system," *Gene*, 91:217-223 (1990).

Leland, *Clinical Virology*, W.B. Saunders Company, Philadelphia, PA at pp. 60-65, and 85-86 (1996).

Maniatis et al., "Regulation of Inducible and Tissue-Specific Gene Expression," *Science*, 236:1237 (1987).

Mizushima and Nagata, "pEF-BOS, a powerful mammalian expression vector," *Nuc. Acids. Res.*, 18:5322 (1990).

Olsen et al., "Isolation of Seven Respiratory Viruses in Shell Vials: a Practical and Highly Sensitive Method," *J. Clin. Microbiol.*, 31:422-425 (1993).

Sambrook et al., *Molecular Cloning: A Laboratory Manual*, 2nd ed., Cold Spring Harbor Laboratory Press, New York, pp. 16.6 16.15 (1989).

Schmidt and Emmons, "General Principles of Laboratory Diagnostic Methods for Viral, Rickettsial, and Chlamydial Infections," in Schmidt and Emmons (eds.), *Diagnostic Procedures for Viral, Rickettsial and Chlamydial Infections*, Washington, D.C.: American Public Health Association, p. 4 (1989).

Uetsuki et al., "Isolation and Characterization of the Human Chromosomal Gene for Polypeptide Chain Elongation Factor-1á," *J. Biol. Chem.*, 264:5791-5798 (1989).

Voss et al., "The role of enhancers in the regulation of cell-type-specific transcriptional control," *Trends Biochem. Sci.*, 11:287-289 (1986).

Wiedbrauk and Johnston, *Manual of Clinical Virology*, Raven Press, Inc., New York, NY, pp. 1-17, and 64-76 (1993).

Drosten, et al., "Identification of a Novel Coronavirus in Patients with Severe Acute Respiratory Syndrome." NeJM 348:1967-976 (2003).

Ksiazek, et al., "A Novel Coronavirus Associated with Severe Acute Respiratory Syndrome." *N Engl J Med*, 348(20), 1953-1966 (2003).

Nakabayashi, et al., "Growth of Human Hepatoma Cells Lines with Differentiated Functions in Chemically Defined Medium." *Cancer Res*, 42(9), 3858-3863 (1982).

Nakabayashi, et al., "Hormonal Control of a-Fetoprotein Secretion in Human Hepatoma Cell Lines Proliferating in Chemically Defined Medium." *Cancer Res*, 45:6379-6383(1985).

Peiris, et al., "Coronavirus as a Possible Cause of Severe Acute Respiratory Syndrome." *Lancet*, 361(9366), 1319-1325 (2003).

Thiel, et al., "Mechanisms and Enzymes Involved in Sars Coronavirus Genome Expression." *J Gen Virol*, 84(Pt 9), 2305-2315 (2003).

DuBridge, et al., "Analysis of Mutation in Human Cells by Using an Epstein-Barr Virus Shuttle System." *Mol Cell Biol*, 7(1):379-387(1987).

Pear, et al., "Production of High-Titer Helper-Free Retroviruses by Transient Transfection." *Proc Natl Acad Sci U S A*, 90(18):8392-8396 (1993).

Wentworth and Holmes "Molecular Determinants of Species Specificity in the Coronavirus Receptor Aminopeptidase N (CD13): Influence of N-Linked Glycosylation." *J Virol*, 75(20):9741-9752 (2001).

Booth, Poutanen, et al., "Clinical Features and Short-Term Outcomes of 144 Patients with Sars in the Greater Toronto Area." *Jama*, 289(21), 2801-2809 (2003).

Database www.lgcpromochem-atcc.com [Online] 'CRL-1696' Cell Biology: ATCC CRL-1696. Product Description for Nov. 7, 2006.

Snijder, et al., "Unique and Conserved Features of Genome and Proteome of SARS-coronavirus, an Early Split-off From the Coronavirus Group 2 Lineage,"*J. Molec. Bio.*, 331:991-1004 (2003).

Schutlz-Cherry, et al., "Mink Lung Epithelial Cells: Unique Cell Line That Supports Influenza A and B Virus Replication," *J. Clin. Microbio.*, 36(12): 3718-3720 (1998).

Tseng, et al., "Apical Entry and Release of Severe Acute Respiratory Syndrome-Associated Coronavirus in Polarized Calu-3 Lung Epithelial Cells." *J Virol*, 79(15):9470-9479 (2005).

Diebel, et al., "Immunoglobulin a Modulates Inflammatory Responses in an in Vitro Model of Pneumonia." *J Trauma*, 59(5):1099-1106 (2005).

Fening, et al., "Calu-3/a-549 Mixed Cells as a Replacement for Primary Rhesus Monkey Kidney Cells for Virus Detection." *J Clin Virol*, 42(3):254-259 (2008).

Foster, et al., "Microparticulate Uptake Mechanisms of in-Vitro Cell Culture Models of the Respiratory Epithelium." *J Pharm Pharmacol*, 53(1):57-66 (2001).

Tumpey, et al., "Characterization of the reconstructed 1918 Spanish influenza pandemic viruses." Science, 310:77-80 (2005).

Lee, et al., "Enhanced Detection of Respiratory Viruses Using the Shell Vial Technique and Monoclonal Antibodies," *J. Virol. Methods*, 39:39-46 (1992).

Brown, *Genomes*, Oxford: Wiley-Liss, p. 179 (1994).

Stryer, *Biochemistry* (3rd ed.), New York: W.H. Freeman and Company, p. 98 (1988).

*The Encyclopedia of Molecular Biology*, Blackwell Science, p. 225 (1994).

Brumback and Wade, "Simultaneous Rapid Culture for Four Respiratory Viruses in the Same Cell Monolayer Using a Differential Multicolored Fluorescent Confirmatory Stain," *J. Clin. Microbiol.*, 34:798-801 (1996).

Huang, et al., "Mink lung cells and mixed mink lung and A549 cells for rapid detection of influenza virus and other respiratory viruses," J. Clin. Microbiol. 38:422-423 (2000).

Melnick, et al, In. *Diagnostic Procedures for Viral and Rickettsia Infections*, by Lennette et al., 4th ed., Amer. Publ. Health Assoc., Inc., Chapter 17, pp. 529, 587, 569, and 570 (1969).

Tadasu Tokumaru, *Diagnostic Procedures for Viral and Rickettsia Infections*, by Lennette et al., 4th ed., Amer. Publ. Health Assoc., Inc., Chapter 19, pp. 641, 654-655, 659 and 660 (1969).

(56) References Cited

OTHER PUBLICATIONS

Barenfanger, et al., "R-Mix cells are faster, at least as sensitive and marginally more costly than conventional cell lines for the detection of respiratory viruses" Journal of Clinical Virology, 22:101-110 (2001).

(St.) George, et al., "Rapid and sensitive detection of respiratory virus infections for directed antiviral treatment using R-Mix cultures" Journal of Clinical Virology, 24:107-115 (2002).

Heggie, et al., "Rapid detection of herpes simplex virus in culture by in situ hybridization," *J. Virol. Meth.*, 41:1-7 (1993).

Lennette, et al., *Diagnostic Procedures for Viral and Rickettsia Infections*, 4th ed., Amer. Publ. Health Assoc., Inc., pp. 653-655, 659-660, and 570-572 (1969).

MacKenzie and McLaren, "Increased Sensitivity for Rapid Detection of Cytomegalovirus by Shell Vial Centrifugation Assay Using Mink Lung Cell Cultures." *J Virol Methods*, 26(2):183-188 (1989).

Matsukura, et al., "[Rantes Expression on Human Bronchial Epithelial Cells]." *Arerugi*, 44(7):715-717 (1995).

Astier-Gin, et al., "Identification of HTLV-I- or HTLV-II-producing cells by cocultivation with BHK-21 cells stably transfected with a LTR-lacZ gene construct." *J. Virological Methods*, 51:19-30 (1995).

Fong, et al., "Advantages of multiple cell culture systems for detection of mixed-virus infections." *J. Virol. Methods*, 33:283-289 (1991).

Benton & Hurst, "Evaluation of mixed cell types and 5-iodo-2'-deoxyuridine treatment upon plaque assay titers of human enteric viruses," Applied and Environmental Microbiology, 51:1036-1040 (1986).

Huang et al., "Application of mixed cell lines for the detection of viruses from clinical specimens," *Clin. Microbiol. Newsletter*, 22:89-92 (2000).

Subrahmanyan et al. "The Development of Double Seeded and Mixed Cell Culture Systems for Use in Diagnostic Virology," *Archiv Fuer Die Gesamte Virusforschung*, 44:291-297 (1974).

Tougianidou et al., "Assessment of Various Cell Lines (including Mixed Cell Cultures) for the Detection of Enteric Viruses in Different Water Sources," *Water Science and Tech.*, 21:311-314 (1989).

Reina et al., "Comparison of Madin-Darby canine kidney cells (MDCK) with a green monkey continuous cell line (Vero) and human lung embryonated cells (MRC-5) in the isolation of influenza A virus from nasopharyngeal aspirates by shell vial culture," *J. Clin. Microbiol.*, 35:1900-1901 (1997).

Database www.lgcpromochem-atcc.com [Online] 'CRL-1848' Cell Biology: ATCC CRL-1848, Nov. 7, 2006.

Castells et al., "NCI-H292 as an Alternative Cell Line for the Isolation and Propagation of the Human Paramyxoviruses," *Arch. Virol.* 115:277-288 (1990).

Chonmaitree et al., "Comparison of Cell Cultures for Rapid Isolation of Enteroviruses," *J. Clin. Microbiol.* 26:2576-2580 (1988).

Dagan and Menegus, "A combination of four cell types for rapid detection of enteroviruses in clinical specimens," *J. Med. Virol.* 19:219-228 (1986).

ELVIS™ Enzyme Linked Virus Inducible System, 1995 catalog page, Diagnostic Hybrids, Inc.

Gleaves et al., "Detection of Human Cytomegalovirus in Clinical Specimens by Centrifugation Culture with a Nonhuman Cell Line," *J. Clin. Microbiol.* 30:1045-1048 (1992).

Hierholzer et al., "Sensitivity of NCI-H292 Human Lung Mucoepidermoid Cells for Respiratory and Other Human Viruses," *J. Clin. Microbiol.* 31:1504-1510 (1993).

Jollick et al., "Typing of HSV with the ELVIS HSV typing system: differential staining characteristics do not result from promoter-transactivator specificity," Abstract, 12th Annual Clinical Virology Symposium, Clearwater FL (1996).

Klespies et al., "Detection of enteroviruses from clinical specimens by spin amplification shell vial culture and monoclonal antibody assay," *J. Clin. Microbiol.* 34:1465-1467 (1996).

Kniazeff et al. "Characteristics of epithelial cells cultured from feline lung," Lab. Invest. 5:495-500 (1976).

Leonardi et al., "Use of Continuous Human Lung Cell Culture for Adenovirus Isolation," *Intervirology* 38:352-355 (1995).

Miller et al. "Clinical virology and viral surveillance in a pediatric group practice: The use of double-seeded tissue culture tubes for primary virus isolation," Am. J. Epidemiol.. 88:245-256 (1969).

Milo et al., "Growth characteristics, morphology, and phospholipid composition of human type II pulmonary alveolar cells grown in a collagen-free microenvironment," In Vitro, 20:899-911 (1984).

Richards et al. "Isolation, biochemical characterization, and culture of lung type II cells of the rat." Lung 165:143-158 (1987).

Robinson et al. "Isolation and culture of human alveolar type II epithelial cells." Am. Rev. Respir. Disease 130:1156-1160 (1984).

Schindler et al., "Investigation of ELVIS Technology for use in HSV Typing of Clinical Specimens," Abstract, 11th Annual Clinical Virology Symposium, Clearwater Beach, FL. May 1, 1995.

ViroMED Laboratories, Inc. Pamphlet entitled, ViroMed Cell Culture Products (1996).

Navarro-Mari, et al. "Rapid Detection of Respiratory Viruses by Shell Vial Assay Using Simultaneous Culture of HEp-2, LLC-MK2, and MDCK Cells in a Single Vial," *J. Clin. Microbiol.*, 37:2346-2347 (1999).

Karetnyi, et al. "Use of a co-cultivation method for detecting cytomegalovirus contamination of cell cultures of simian origin," *Voprosy Virusdogii*, 27(2), Abstract (1982).

Rangan, et al. "Detection and assay of feline leukemia virus (FeLV) by a mixed culture cytopathogenicity method," *Virol.*, 47:247-250 (1972).

Barenfanger, et al., "Combination of Mixed Cell Lines Mix A and Mix B Supports Growth of All Clinical Enterovirus Isolates Tested" (2000).

Huang et al., "CV-1/MRC-5 mixed cells for detection of herpes simplex viruses: comparison with primary rabbit kidney and mink lung cells." Clinical Virology Symposium (May 9-12, 1999).

Huang et al., Clinical Virology Symposium, Sensitive cell lines for detection of respiratory viruses from primary rhesus monkey kidney and HEP-2 cells (Apr. 26-29, 1998).

Huang, "Rapid detection of respiratory viruses and enteroviruses using mixtures of continuous cells," Pan Am. Soc. Clin. Virol. 25:1-4 (Nov. 1998).

Ahmed, et al., "Characterization of a Retrovirus Isolated from Normal Mink Cells Co-cultivated with a Dog Mammary Tumour." J. Gen. Virol., 42:179-184 (1979).

Fouchier, et al., "Aetiology: Koch's Postulates Fulfilled for SARS Virus." Nature, 423(6937):240 (2003).

Gillim-Ross, et al., "Discovery of Novel Human and Animal Cells Infected by the Severe Acute Respiratory Syndrome Coronavirus by Replication-Specific Multiplex Reverse Transcription-PCR." J Clin Microbiol, 42(7):3196-3206 (2004)R.

Goldstein, et al., "Evaluation of Three Cell Culture Systems as Substrates for Influenza Virus Assay." Appl Microbiol, 19(4):580-582 (1970).

Hatakeyama, et al., "Enhanced Expression of an Alpha2,6-Linked Sialic Acid on MDCK Cells Improves Isolation of Human Influenza Viruses and Evaluation of Their Sensitivity to a Neuraminidase Inhibitor." J Clin Microbiol, 43(8):4139-4146 (2005).

Matrosovich, et al., "Overexpression of the Alpha-2,6-Sialyltransferase in Mdck Cells Increases Influenza Virus Sensitivity to Neuraminidase Inhibitors." J Virol, 77(15):8418-8425 (2003).

Stamm, et al., "Detection of Chlamydia trachomatis Inclusions in McCoy Cell Cultures with Fluorescein-Conjugated Monoclonal Antibodies." Journal of Clinical Microbiology, 17:666-668 (1983).

* cited by examiner

MIXED CELL DIAGNOSTIC SYSTEMS FOR DETECTION OF RESPIRATORY, HERPES AND ENTERIC VIRUSES

This is a continuation of, and claims priority under 35 U.S.C. §111(a) to, co-pending U.S. Ser. No. 13/409,952 filed on Mar. 1, 2012, which is a continuation of U.S. Ser. No. 12/253,127 filed on Oct. 16, 2008 and issued as Pat. No. 8,142,997, which is a continuation of U.S. Ser. No. 11/414,760 filed on Apr 28, 2006 and issued as U.S. Pat. No. 7,442,508, which is a continuation of U.S. Ser. No. 11/231,552 filed on Sep. 20, 2005 and now abandoned, which is a continuation-in-part of U.S. application Ser. No. 10/813,852, filed Mar. 30, 2004 now issued as U.S. Pat. No. 6,946,291, which is a continuation-in-part of U.S. application Ser. No. 10/407,789, filed Apr. 4, 2003, now U.S. Pat. No. 6,875,600, which is a continuation of U.S. application Ser. No. 09/927,481, filed Aug. 9, 2001, now U.S. Pat. No. 6,573,080, which is a continuation of U.S. application Ser. No. 09/661,849, filed Sep. 14, 2000, now U.S. Pat. No. 6,376,172, which is a divisional of U.S. application Ser. No. 09/066,072, filed Apr. 24, 1998, now U.S. Pat. No. 6,168,915, the contents of which are incorporated in their entirety for all purposes.

FIELD OF THE INVENTION

The present invention generally relates to the field of diagnostic microbiology, and more particularly, to compositions and methods for detecting and differentiating one or more viruses or other intracellular parasites present in a specimen. The present invention also provides compositions and methods to evaluate the susceptibility of organisms to antimicrobial agents.

BACKGROUND OF THE INVENTION

Despite recent advances in methods for the detection of viruses using molecular methods, the detection and identification of these organisms in cell culture remains the "gold standard" by which most viral diseases are definitively diagnosed, and against which newer methods are compared (See e.g., Wiedbrauk and Johnston, *Manual of Clinical Virology*, Raven Press, Inc., New York, N.Y. [1993], pp. 1-17). Cell cultures are also used for the detection and identification of other intracellular parasites, especially obligate intracellular parasites such as *Chlamydia* and *Rickettsia*.

There are two general types of cell culture methods used for virus identification. The first method uses identification of virus-induced cytopathic effect (CPE) as an endpoint for virus detection. The second method utilizes molecular methods to identify the presence of virus before CPE is evident in the infected cultures. Both methods utilize cell cultures, which may present problems for small laboratories with limited expertise in cell culturing methods, space, funding, equipment, and supplies. Depending upon the cells used, cell cultures can be difficult to maintain and often require the efforts of skilled laboratorians. In addition, cell cultures require equipment such as cell culture hoods, inverted microscopes (for observation of cells), incubators with $CO_2$ lines, and other equipment not readily available in many laboratories.

CPE-Based Tests

CPE-based tests often require long incubation times, as virus-induced CPE only becomes evident after multiple rounds of viral replication and spread of virus to neighboring cells (i.e., the cells are "permissive" for viral infection). Virus spread results in the destruction of the cells surrounding the cell originally infected. CPE-based tests have been traditionally conducted in tubes or flasks containing a single cell type that is adhered or anchored to the sides and/or bottom of the tube or flask. As the virus must infect a cell, replicate, and spread to neighboring cells in which the process is repeated, results can be delayed for at least 28 days. Indeed, results are often not available for 7-28 days after inoculation of the cell culture with the virus suspension (See e.g., Leland, *Clinical Virology*, W.B. Saunders, Philadelphia [1996], pp. 60-65). The time necessary to establish visible CPE is dependent upon the rate of viral replication, which can vary among cell types and viruses. Thus, the amount of time needed to detect virus in a sample can greatly vary.

Pre-CPE Tests

In contrast to CPE-based tests, pre-CPE tests require only entry of the virus into a susceptible host cell and detectable expression of at least one early virus-specific antigen or nucleic acid. Detection of the virus-specific analyte or other indicator is accomplished by a number of methods (e.g., labeled antibodies, the polymerase chain reaction [PCR], or the use of other reporters, such as the ELVIS™ system). Expression of early viral genes has been shown to be very rapid in many virus-host cell systems in vitro. Thus, use of pre-CPE based virus tests significantly reduces the time required to detect and identify viruses in clinical specimens.

Pre-CPE detection of virus is often accomplished by using monolayers of adherent cells grown on 12 mm round coverslips contained in 1 dram shell vials (i.e., the "shell vial" method or technique). The shell vial technique uses centrifugation of the specimen to force viral introduction into cells and enhance viral isolation. These vials are prepared by dispensing cells into sterile shell vials containing coverslips. The vials are incubated in an upright position until the cells form a monolayer on the coverslip. For shell vial inoculation, the culture medium is decanted from the vial, processed sample (i.e., the clinical specimen) is added to the cell monolayer, and the vial is centrifuged at low speed, often for one hour. After centrifugation, fresh culture medium is added to each vial. The vials are then incubated for the desired period of time. At the end of the incubation period, the coverslips are stained using an antigen detection method (e.g., immunofluorescence) or the cells are evaluated via molecular diagnostic techniques.

In addition to viruses, shell vials are also commonly used for the detection and identification of *Chlamydia*, as other methods available for the detection and identification of these organisms are quite cumbersome, as well as time and reagent-consuming (See e.g., Wiedbrauk and Johnston, supra, pp. 64-76).

The major advantage of these pre-CPE testing methods is that rapid test results are often possible. One major disadvantage to pre-CPE testing of shell vial cultures is that this type of test is feasible and cost-effective only if one or a few viral agents are sought for identification, and if a high proportion of specimens are likely to be positive. For a review see for instance, Schmidt and Emmons (eds.), "General Principles of Laboratory Diagnostic Methods for Viral, Rickettsial and Chlamydial Infections," *Diagnostic Procedures for Viral, Rickettsial and Chlamydial Infections*, American Public Health Association, Washington, D.C., [1989], p. 4.

Clinical Specimens

For example, the presence of skin vesicles in the genital area of a patient is highly suspicious for infection by herpes simplex virus (HSV). Typically, the physician will obtain a specimen from the affected region (i.e., a vesicle) and order a CPE or a pre-CPE virus test on a single, HSV-susceptible cell line. These cell lines are often supplied in tubes, shell vials or multi-well plates (e.g., microtiter plates). After inoculation of the cell line and an appropriate incubation time, confirmation of the presence of HSV in the sample can be accomplished using one or more of the many analytical methods (e.g., immunofluorescence, immunoperoxidase, nucleic acid probes, or substrates for virus-induced reporter genes).

For detection of cytomegalovirus (CMV), shell vials containing cells from a single cell line (e.g., human fibroblast cell lines, such as lung [MRC-5 cells] or foreskin [HFF] cells) are often used. The cells are grown to confluency on the coverslip within the vial, the sample is added to the vial, the vial is incubated for 24-48 hours or longer, and an immunofluorescent method is used to detect expression of CMV early antigen.

Accurate differential diagnosis is significantly more difficult in virus diseases due to respiratory, gastrointestinal, genital, or parenteral routes of transmission because many pathogenic viruses are capable of eliciting similar symptoms or the infection is sub-clinical (i.e., the signs and symptoms are not readily apparent).

Of the respiratory viruses, rhinoviruses and corona viruses are responsible for a large proportion of upper respiratory infections. Once these viruses reach the upper respiratory mucosa, they attach to and infect epithelial cells. Typically, these infections last only a few days and self-resolve. Other respiratory viruses, such as the influenzas, parainfluenzas, respiratory syncytial virus (RSV), and various adenoviruses attach to and infect ciliated, columnar epithelial cells. The virus-infected cells lyse, resulting in the release of enzymes and activate complement, resulting in a local mononuclear inflammatory response. Normal airway clearance mechanisms fail because of the failure of the epithelial cells to function normally. These cells may also slough off. Cell debris from dead and dying cells often obstructs airways, and the host becomes very susceptible to secondary bacterial infection and/or superinfection. All of these viruses may progress to lower respiratory involvement and pneumonia. After replication in the respiratory epithelial cells, adenovirus may travel via the blood to the lymphoid tissues in all areas of the body, causing systemic infection or disease.

Standard clinical virology practice is to inoculate multiple tubes of cell cultures with the specimen (e.g., throat swab, nasopharyngeal swab, or sputum specimen) as the tropism of each type of virus for specific cell types is often very narrow (i.e., only one type of virus may grow optimally on a single cell type). This narrow tropism of virus for a limited number of cell types creates at least two major practical problems for both CPE and pre-CPE virus testing.

First, primary monkey kidney cells are currently the cell line of choice for isolation of influenza viruses. The manufacture of these cells requires the quarantine of source animals for long periods prior to sacrifice and cell culture preparation. This quarantine period is used to monitor the animals for good health and allows time to test the animals for infection by endogenous simian viruses such as foamy virus, SV5, and SV40. The quarantine period also greatly reduces, but does not eliminate, the possibility that the monkeys are infected with Monkey B Virus, a herpesvirus that is highly fatal to humans. In addition, there are other problems related to the use of monkeys for the production of primary cell cultures, including the reduction in the stock of suitable animals due to importation concerns and monkey population considerations.

Second, additional continuous cell lines are required in order to detect respiratory viruses other than influenza virus. Thus, multiple cell lines are used in order to diagnose the viral infection/disease of each patient. The need for multiple units of individual cell lines is compounded in methods using pre-CPE tests for detection and identification of respiratory viruses. Pre-CPE testing for respiratory viruses requires the expenditure of significant labor in handling coverslips, the added expense of molecular reagents used with multiple cell lines for both positive and negative specimens, and the significant labor associated with microscopically reading each of the multiple cell lines inoculated in the panel of cell lines.

However, despite these drawbacks, shell vial technology using single cell types in multiple units (tubes, shell vials, etc.), is still currently used to detect respiratory viruses, as it is a proven method. For example, detection of RSV in 16 hours using shell vials containing only HEp-2 cells yielded more positives than antigen detection methods applied directly to the clinical specimen, and as many positives as conventional cell cultures (Smith et al., J. Clin. Microbiol., 29:463-465 [1991]). Isolation of other respiratory viruses has also been possible with shell vial cultures containing a monolayer of a single cell type. For example, using vials of primary monkey kidney cells and A549 cells incubated for 40 hours, 83% of adenoviruses, 94% of influenza B, and 80% of parainfluenza virus types 1, 2, and 3 were identified (Rabalais et al., J. Clin. Microbiol., 30:1505-1508 [1992]). In another report, 50% of adenoviruses, 94% of influenza A viruses, 100% of influenza B viruses, and 100% of parainfluenza viruses, in shell vials of primary rhesus monkey kidney cells, and 92% of RSV in shell vials of HEp-2 cells incubated for 2-4 days (See e.g., Olsen et al., J. Clin. Microbiol., 31:422-425 [1993]; and Leland, *Clinical Virology*, W.B. Saunders Company, Philadelphia, Pa. [1996], at p. 85-86).

Although these methods provide relatively rapid results (i.e., as opposed to the long incubation periods often necessary for CPE tests), there remains a need in clinical and reference virology laboratories for cell culture methods and compositions for the reliable detection and identification of viruses, in a single, easy-to-manipulate unit. Preferred methods and compositions provide a means for rapid viral detection and identification in a cost-effective manner, while also providing the sensitivity of a diagnostic assay system.

SUMMARY OF THE INVENTION

The present invention generally relates to the field of diagnostic microbiology, and more particularly, to compositions and methods for detecting and differentiating one or more viruses or other intracellular parasites present in a specimen. The present invention also provides compositions and methods to evaluate the susceptibility of a organisms to antimicrobial agents.

In particular, the present invention provides methods and compositions suitable for the detection of viruses using CPE-based and pre-CPE methods. The preferred embodiments encompass mixed cell cultures, which contain at least two different cell types. In some preferred embodiments, the mixed cell cultures contain two different cell types, while in other embodiments, the mixed cell cultures contain three or more different cell types. Thus, it is intended that the present invention encompass compositions in which at least two cell types are mixed together in one container (e.g., flask, tube, shell vial, or any other container suitable for the growth of cells). Importantly, each cell type within these mixed cell cultures retains its susceptibility to viruses and other intracellular parasites as if it was in a single cell culture (i.e., a cell culture that contains only one cell type, as known in the art). In addition, the mixed cell cultures of the present invention remain viable for as long as required for their use in diagnostic assays. In particularly preferred embodiments, the cell types included within mixed cell cultures are present in approximately the same ratio (i.e., for a two cell type mixed, there is a 50:50 ratio of cell types). However, it is not intended that the present invention be limited to any particular ratio of cell types in mixed culture, as various detection systems may be optimized using different ratios. For example, in some circumstances, a two cell mixture of 45:55, 40:60, or even 35:75, may be more suited than a 50:50 ratio.

The present invention also provides methods and compositions suitable for the detection and identification of non-viral obligate intracellular and intracellular parasites, such as members of the Chlamydiales and Ricketsiales.

The present invention also contemplates compositions comprising a cell culture suitable for the detection of intracellular parasites, wherein the cell culture comprises at least two cell types susceptible to infection by at least one intracellular parasite. In some preferred embodiments of the composition, the cell types comprise a first cell type and a second cell type. In some embodiments, the first cell type consists of buffalo green monkey kidney cells and the second cell type consists of mink lung cells. In other embodiments, the first cell type consists of mink lung cells and the second cell type consists of human mucoepidermoid cells. In yet other embodiments, the first cell type consists of human lung carcinoma cells and the second cell type consists of human mucoepidermoid cells. In still other embodiments, the first cell type consists of buffalo green monkey kidney cells and the second cell type consists of human embryonic lung cells. In further embodiments, the cell type consists of human epidermoid laryngeal carcinoma cells and the second cell type consists of McCoy cells. In additional embodiments, the first cell type consists of mink lung cells and the second cell type consists of human diploid lung cells.

In some preferred embodiments, the cell types of the composition are susceptible to respiratory viruses, including but not limited to influenza viruses of any type (e.g., Influenza A, Influenza B, and Influenza C) and/or strain, RSV, cytomegalovirus, parainfluenza viruses, respiratory syncytial virus, rhinoviruses, coronaviruses, and adenoviruses. In yet other embodiments, the cell types of the composition are susceptible to enteroviruses, including but not limited to any type and/or strain of echovirus, poliovirus, and Coxsackie virus (e.g., Coxsackie A and B viruses), and numbered EV strains. In addition to enteroviruses, it is contemplated that the present invention encompasses cell types that are susceptible to picornaviruses such as Hepatitis A.

The present invention also provides methods for the detection and identification of intracellular parasites in a sample, comprising the steps of: providing a sample suspected of containing one or more intracellular parasites, and a mixed cell culture comprising at least two cell types; inoculating the mixed cell culture with the sample to produce an inoculated culture; and observing the inoculated culture for the presence of the one or more intracellular parasites.

In some embodiments of the method, the intracellular parasite is a virus. In some particularly preferred embodiments, the virus is selected from the group consisting of cytomegalovirus, influenza viruses, parainfluenza viruses, respiratory syncytial virus, rhinoviruses, coronaviruses, and adenoviruses. In yet other embodiments of the methods, the virus is an enterovirus. In other particularly preferred embodiments, the enterovirus is selected from the group consisting of poliovirus, Coxsackie viruses and echoviruses (e.g., Coxsackie A and B viruses), and numbered EV strains. In addition to enteroviruses, it is contemplated that the present invention encompasses cell types that are susceptible to picornaviruses such as Hepatitis A. In still other preferred embodiments, the virus is a herpes virus. In other particularly preferred embodiments, the herpes virus is selected from the group consisting of Herpes Simplex Type 1, Herpes Simplex Type 2, Cytomegalovirus, Varicella-Zoster virus, Epstein-Barr virus, Human Herpes Virus 6, Human Herpes Virus 7, and Human Herpes Virus 8. In yet other preferred embodiments, the intracellular parasite is a member of the genus *Chlamydia*. In still other particularly preferred embodiments, the intracellular parasite is *C. trachomatis*.

In some preferred embodiments of the methods, the cell types comprise a first cell type and a second cell type. In some preferred embodiments, the first cell type is a mink lung cell, and the second cell type is a human mucoepidermoid cell. In other preferred embodiments, the first cell type is a buffalo green monkey kidney cell and the second cell type is a human mucoepidermoid cell. In yet another alternative embodiment, the first cell type is a genetically engineered baby hamster kidney cell and the second cell type is a mink lung cell. In still other embodiments, the first cell type is a first genetically engineered cell type and the second cell type is a second genetically engineered cell type.

It is contemplated that the methods of the present invention will be used in conjunction with controls of known positivity and negativity for the virus(es) and/or other intracellular organism of interest.

The present invention also provides methods for the detection and identification of intracellular parasites in a sample, comprising the steps of providing: a sample suspected of containing one or more intracellular parasites, and a mixed cell culture comprising a first cell type and a second cell type; inoculating the mixed cell culture with the sample to produce an inoculated culture; and observing the inoculated culture for the presence of the one or more intracellular parasites.

In some particularly preferred embodiments, the intracellular parasite is a virus. In some particularly preferred embodiments, the virus is selected from the group consisting of cytomegalovirus, influenza viruses, parainfluenza viruses, respiratory syncytial virus, rhinoviruses, coronaviruses, and adenoviruses. In yet other embodiments of the methods, the virus is an enterovirus. In other particularly preferred embodiments, the enterovirus is selected from the group consisting of poliovirus, Coxsackie viruses and echoviruses (e.g., Coxsackie A and B viruses), and numbered EV strains. In addition to enteroviruses, it is contemplated that the present invention encompasses cell types that are susceptible to picornaviruses such as Hepatitis A. In still other preferred embodiments, the virus is a herpes virus. In other particularly preferred embodiments, the herpes virus is selected from the group consisting of Herpes Simplex Type 1, Herpes Simplex Type 2, Cytomegalovirus, Varicella-Zoster virus, Epstein-Barr virus, Human Herpes Virus 6, Human Herpes Virus 7, and Human Herpes Virus 8. In yet other preferred embodiments, the intracellular parasite is a member of the genus *Chlamydia*. In still other particularly preferred embodiments, the intracellular parasite is *C. trachomatis*.

In some preferred embodiments of the methods, the cell types comprise a first cell type and a second cell type. In some preferred embodiments, the first cell type is a mink lung cell, and the second cell type is a human mucoepidermoid cell. In other preferred embodiments, the first cell type is a buffalo green monkey kidney cell and the second cell type is a human mucoepidermoid cell. In yet another alternative embodiment, the first cell type is a genetically engineered baby hamster kidney cell and the second cell type is a mink lung cell. In still other embodiments, the first cell type is a first genetically engineered cell type and the second cell type is a second genetically engineered cell type.

It is contemplated that the methods of the present invention will be used in conjunction with controls of known positivity and negativity for the viruses) and/or other intracellular organism of interest.

The present invention further provides methods for the detection of influenza virus, comprising the steps of providing a sample suspected of containing influenza virus, and mink lung cells; inoculating the mink lung cells with the sample; and detecting the presence of the influenza within the mink lung cells. In particularly preferred embodiments, the mink lung cells are Mv1Lu cells. In alternative embodiments, the influenza virus is selected from the group consisting of Influenza A, Influenza B, and Influenza C.

It is contemplated that the methods of the present invention will be used in conjunction with controls of known positivity and negativity for the virus(es) and/or other intracellular organism of interest.

In one embodiment, the present invention provides methods for the detection of infectious virus in a specimen comprising the steps of: a) providing a specimen suspected of containing a virus, a cell line permissive for infection by the virus, and a genetically engineered cell line containing an oligonucleotide having a sequence comprising a promoter sequence derived from the virus, wherein the promoter sequence is operably linked to a reporter gene, and wherein the expression of the reporter gene is dependent upon and quantitatively proportional to the presence of the virus; b) mixing together the permissive cell line and the genetically engineered cell line to create a mixed cell culture; c) inoculating the mixed cell culture with the specimen under conditions which permit the infection of the mixed cell culture by the virus; and d) detecting the expression of the reporter gene and thereby detecting the presence of virus in the specimen. In one preferred embodiment, the mixed cell culture is a mixture consisting of 80-99% of the permissive cell line and 1-20% of the genetically engineered cell line. In other preferred embodiments, the mixed cell culture is a mixture consisting of equal proportions of the cell types used in the mixture.

In one embodiment of the method, the genetically engineered cell line contains an oligonucleotide having a sequence comprising a herpesvirus inducible promoter operably linked to a reporter gene selected from the group comprising the *Escherichia coli* lacZ gene and a luciferase gene. In one preferred embodiment of the method, the genetically engineered cell line is BHKICP10LacZ. In an alternative preferred embodiment, the genetically engineered cell line is BHKICP6LacZ. However, it is not intended that the reporter gene be limited to the lacZ and luciferase genes. Indeed, it is contemplated that any suitable reporter gene known to those in the art will be useful in the method of the present invention.

It is also contemplated that various permissive cell lines will be useful in the method of the present invention. In one embodiment, the permissive cell line is permissive for infection with herpesvirus. In a particularly preferred embodiment, the permissive cell line is MRC-5.

It is contemplated that the method, of the present invention will be used in conjunction with controls of known positivity and negativity for the virus(es) of interest. Thus, for mixed cultures in which genetically engineered cell lines are used, it is contemplated that the pattern of reporter gene expression present in a test sample (e.g., from a clinical specimen) will be compared to the patterns of reporter gene expression in control samples known to be positive and/or negative for the virus(es) of interest. It is also contemplated that effects unrelated to the expression of the reporter gene will be detectable, including but not limited to CPE. These effects, alone and in combination with the reporter gene expression may be used to detect the presence of viral infection.

The present invention also provides methods for the typing of infectious herpesvirus in specimens, comprising the steps of: a) providing a specimen suspected of containing one or more members of the herpesvirus family, a cell line permissive for infection by one or more members of the herpesvirus family, a genetically engineered cell line containing an oligonucleotide having a sequence comprising a promoter sequence derived from a member of the herpesvirus family wherein the promoter sequence is operably linked to a reporter gene, and the expression of the reporter gene is dependent upon and quantitatively proportional to the presence of herpesvirus and wherein the expression of the reporter gene varies in a distinguishable manner as a result of the presence of different members of the herpesvirus family; b) mixing together the permissive cell line and the genetically engineered cell line to create a mixed cell culture; c) inoculating this mixed cell culture with the specimen under conditions which permit the infection of the mixed cell culture by members of the herpesvirus family, wherein the infection results in a distinguishable pattern of expression by the reporter gene; d) detecting the expression of the reporter gene and thereby detecting the presence of one or more members of the herpesvirus family in the specimen; and e) identifying the presence of a specific member of the herpesvirus family based upon the resulting distinguishable pattern. It is contemplated that this pattern of expression will be observable by various assisted and non-assisted methods, including visual observation by eye, spectrophotometric observation, etc. It is not intended that the detection of distinguishable pattern(s) be limited to any particular method of detection.

In a preferred embodiment of the typing method of the present invention, the mixed cell culture is a mixture consisting of 80-99% of the permissive cell line and 1-20% of the genetically engineered cell line. In yet other preferred embodiments, the cell types are in approximate equal proportions in the mixed cell cultures. As with the first method described, it is not intended that the present invention be limited to any particular herpesvirus. In one particular embodiment, the member of the herpesvirus family detected and typed using the method of the present invention is selected from the group comprising HSV-1, HSV-2, CMV, VZV, EBV, and human herpes viruses such as HHV-6, HHV-7, and HHV-8. It is intended that one or more herpesviruses may be detected and typed in one specimen. In this manner, co-infection with multiple herpesviruses may be diagnosed. For example, it is contemplated that mixed infections with HSV-1 and HSV-2 may be detectable and the infections distinguished using the methods of the present invention.

In one embodiment of the typing method, the reporter gene comprises *E. coli* lacZ gene. However, it is not intended that the reporter gene be limited to lacZ. Indeed, it is contemplated that any reporter gene may be used in this method. In one particularly preferred embodiment, the detection of the reporter gene is accomplished through by histochemical staining. It is contemplated that one member of the herpesvirus family will produce an histochemically pattern of expression that is distinguishable from the histochemical patterns produced by other members of the herpesvirus family. In this manner, it is possible to use the methods of the present invention to distinguish infection with one herpesvirus from infection with another herpesvirus.

It is contemplated that the method of the present invention will be used in conjunction with controls of known positivity and negativity for the virus(es) of interest. Thus, it is contemplated that the pattern of expression present in a test sample (e.g., from a clinical specimen) will be compared to the patterns of expression in control samples known to be positive and/or negative for the virus(es) of interest. It is also contemplated that effects unrelated to the expression of the reporter gene will be detectable, including but not limited to CPE. These effects, alone and in combination with reporter gene expression may be used to detect the presence of viral infection, as well as provide information to distinguish between viruses.

In yet another embodiment, the present invention provides a composition comprising a mixed cell culture, wherein the mixed cell culture comprises the combination of a genetically engineered cell line transformed with a promoter sequence from a virus, wherein the promoter sequence is operably linked to a reporter gene, and wherein expression of the reporter gene is dependent upon and quantitatively proportional to the presence of virus, and a non-engineered cell line which is permissive for virus infection.

In one embodiment of the composition, the mixed cell culture is a mixture consisting of 1-20% of the genetically engineered cell line and 80-99% of the permissive cell line. In yet other preferred embodiments, the cell types are in approximate equal proportions in the mixed cell cultures. In one preferred embodiment of the composition, the genetically engineered cell line component may comprise a promoter for a gene that encodes ribonucleotide reductase. In an alternative preferred embodiment, the promoter may comprise genes that encode one or more subunits of ribonucleotide reductase. In one particularly preferred embodiment, the genetically engineered cell line is BHKICP10LacZ, while in another particularly preferred embodiment, the genetically engineered cell line is BHKICP6LacZ. In an alternative embodiment of the composition, the genetically engineered cell line comprises an *E. coli* lacZ gene positioned 3' to a virus inducible promoter. It is contemplated that this lacZ gene be positioned immediately 3' to this virus-inducible promoter. However, it is not intended that these sequences will be contiguous. Indeed, it is contemplated only that the reporter and promoter genes are operably linked. Furthermore, it is contemplated that the composition will comprise promoter sequences from any virus, including but not limited to members of the herpesvirus family. It is also contemplated that the non-engineered cell line be permissive for infection by any number of viruses, including but not limited to members of the herpesvirus family.

In one preferred embodiment, the composition includes a genetically engineered cell line, which includes a promoter for a gene that encodes a ribonucleotide reductase large subunit and the virus is a member of the herpesvirus family selected from the group consisting of HSV-1, HSV-2, CMV, VZV, EBV, HHV-6, HHV-7, and HHV-8. However, it is not intended that the present invention be limited to any particular herpesvirus. In one preferred embodiment, the genetically engineered cell line component contains an ICP10 promoter and the herpesvirus family member is HSV-2, while in another preferred embodiment, the genetically engineered cell line comprises an ICP6 promoter and the herpesvirus family member is HSV-1.

It is contemplated that the detection of reporter gene expression be accomplished through various methods, including, but not limited to colorimetric, fluorimetric or luminometric assays or assay systems. In one preferred embodiment, the reporter gene encodes-galactosidase.

In one embodiment, the composition includes a genetically engineered cell line that is a mammalian cell line susceptible to infection by virus. In one preferred embodiment, the genetically engineered cell line comprises baby hamster kidney cells (e.g., cell lines derived from BHK cells). In one embodiment, the composition includes a permissive cell line that is permissive to infection by herpesviruses, including but not limited to HSV-1 and HSV-2. In a particularly preferred embodiment, the permissive cell line is MRC-5. It is not intended that the composition of the present invention be limited to detection of viral infection based on the expression of the reporter gene, as effects such as CPE may also be detectable.

The present invention also provides a kit for assaying for the presence of infectious herpesvirus in a specimen. The kit includes: a) a supply of a mixed cell line comprised of a cell line of genetically engineered mammalian cells susceptible to infection by herpesvirus, wherein the cell line contains an oligonucleotide having a sequence comprising a virus promoter sequence operably linked to a reporter gene, and where the expression of the reporter gene is dependent upon and quantitatively proportional to the presence of virus in the specimen; and a cell line permissive for virus; and b) a supply of reagents to detect the expression of the reporter gene. It is not intended that the promoter sequences present within the genetically engineered cell line be limited to any particular virus or virus family. It is contemplated that any virus promoter will be useful in the kit of the present invention. However, in one preferred embodiment, herpesvirus promoter sequences are present in the genetically engineered cell line.

It is contemplated that various promoter sequences will be useful in the kit of the present invention. However, in a preferred embodiment, the promoter encodes either a complete ribonucleotide reductase enzyme, or in the alternative, subunits of ribonucleotide reductase. In one particularly preferred embodiment, the promoter sequence contains a promoter for a gene that encodes a ribonucleotide reductase large subunit and the herpesvirus is a herpesvirus family member selected from the group consisting of HSV-1, HSV-2, CMV, VZV, EBV, HHV-6, HHV-7, and HHV-8. However, it is not intended that the kit will be limited to this list of herpesviruses. Indeed, it is contemplated that any herpesvirus may be detected using the present kit. In one particularly preferred embodiment of the kit, the promoter, sequence contains an ICP10 promoter and the herpesvirus family member is HSV-2, while in an alternative preferred embodiment, the promoter sequence contains an ICP6 promoter and the herpesvirus family member is HSV-1.

In one preferred embodiment of the kit, the promoter sequence present in the genetically engineered cell line comprises an *E. coli* lacZ gene that is operably linked to a herpesvirus inducible promoter. In one particularly preferred embodiment, the genetically engineered mammalian cells are BHKICP10LacZ cells, while in an alternative embodiment the cells are BHKICP6LacZ cells.

In one preferred embodiment, the reporter gene encodes-galactosidase. However, it is not intended that the present invention be limited to any particular reporter gene. It is also contemplated that the reporter gene will encode any number of enzymes that are amenable to detection by various methods, including but not limited to such methods as colorimetric, fluorimetric or luminometric assay systems. In one preferred embodiment of the kit, the reagents provided for the detection of reporter gene expression may include, but are not limited to, solutions of 5-bromo-4-chloro-3-indolyl-D-galactopyranoside, o-nitrophenyl-galactopyranoside solution, and fluorescein di-D-galactopyranoside. However, it is not intended to limit the kit to these assay systems, as other systems (e.g., radiometric assay systems) may be useful.

It is contemplated that the kit of the present invention may also include additional components, such as materials suitable for positive and negative controls and instructions for use. It is not intended that the kit of the present invention be limited to the mixed cell line and reagents for the detection of reporter gene expression. It is also intended that the kit will be useful for detection of viral effects on cells other than and unrelated to reporter gene expression. For example, it is contemplated that the kit may be useful for detection of CPE.

In a further embodiment, the invention provides a composition comprising a mixed cell culture comprising MDCK cells and one or more of A549 cells and H292 cells. These compositions are useful in detecting the presence of one or more of influenza viruses (such as influenza A and/or B), respiratory syncytial virus (RSV), adenovirus, parainfluenza 1 virus, parainfluenza 2 virus, parainfluenza 3 virus, and metapneumovirus. These methods are also useful in producing one or more of influenza viruses (such as influenza A and/or B), respiratory syncytial virus (RSV), adenovirus, parainfluenza 1 virus, parainfluenza 2 virus, and parainfluenza 3 virus.

Also provided herein is a method for detecting influenza virus, comprising: 1) providing: a) mixed cell culture comprising MDCK cells and one or more of A549 cells and H292 cells; and b) a sample; 2) inoculating the mixed cell culture with the sample to produce an inoculated culture; and 3) detecting the presence of influenza virus. In one embodiment, the level of permissivity and/or susceptibility of the MDCK cells to severe acute respiratory syndrome coronavirus is 0.004% the level of permissivity and/or susceptibility of Mv1Lu cells to severe acute respiratory syndrome coronavirus. In a further embodiment, the influenza virus comprises one or more of influenza A virus and influenza B virus. In another embodiment, the mixed cell culture comprises MDCK cells and A549 cells, and the method optionally further comprises detecting the presence of one or more of respiratory syncytial virus (RSV), adenovirus, parainfluenza 1 virus, parainfluenza 2 virus, parainfluenza 3 virus, and metapneumovirus. In an alternative embodiment, the mixed cell culture comprises MDCK cells and H292 cells, and the method optionally further comprises detecting the presence of one or more of respiratory syncytial virus (RSV), adenovirus, parainfluenza 1 virus, parainfluenza 2 virus, parainfluenza 3 virus, and metapneumovirus. In a further embodiment, the mixed cell culture comprises MDCK cells, A549 cells, and H292 cells, and the method optionally further comprises detecting the presence of one or more of respiratory syncytial virus (RSV), adenovirus, parainfluenza 1 virus, parainfluenza 2 virus, parainfluenza 3 virus, and metapneumovirus.

Also provided by the invention is a method for producing influenza virus, comprising: 1) providing: a) mixed cell culture comprising MDCK cells and one or more of A549 cells and H292 cells; and b) a sample; 2) inoculating the mixed cell culture with the sample to produce an inoculated culture, wherein the inoculated culture produces influenza virus. In one embodiment, the influenza virus comprises one or more of influenza A virus and influenza B virus. In another embodiment, the mixed cell culture comprises MDCK cells and A549 cells, and the method optionally further comprises producing one or more of respiratory syncytial virus (RSV), adenovirus, parainfluenza 1 virus, parainfluenza 2 virus, parainfluenza 3 virus, and metapneumovirus. Alternatively, the mixed cell culture comprises MDCK cells and H292 cells, and the method optionally further comprises producing one or more of respiratory syncytial virus (RSV), adenovirus, parainfluenza 1 virus, parainfluenza 2 virus, parainfluenza 3 virus, and metapneumovirus. In yet another alternative, the mixed cell culture comprises MDCK cells, A549 cells, and H292 cells, and the method further comprises producing one or more of respiratory syncytial virus (RSV), adenovirus, parainfluenza 1 virus, parainfluenza 2 virus, parainfluenza 3 virus, and metapneumovirus.

Also provided is a method for detecting metapneumovirus, comprising: 1) providing a) a mixed cell culture comprising MDCK cells and A549 cells; and b) sample; 2) inoculating the mixed cell culture with the sample to produce inoculated cells; and 3) detecting the presence of metapneumovirus. In one embodiment, the method further comprises detecting influenza virus, as exemplified by influenza B virus and/or influenza A virus. In another embodiment, the method further comprises detecting the presence of one or more of respiratory syncytial virus (RSV), adenovirus, parainfluenza 1 virus, parainfluenza 2 virus, and parainfluenza 3 virus. In an alternative embodiment, the mixed cell culture further comprises H292 cells, and the method optionally further comprises detecting the presence of one or more of respiratory syncytial virus (RSV), adenovirus, parainfluenza 1 virus, parainfluenza 2 virus, and parainfluenza 3 virus.

The invention also provides a method for producing metapneumovirus, comprising: 1) providing a mixed cell culture comprising MDCK cells and A549 cells; and b) sample; 2) inoculating the cultured cells with the sample to produce inoculated an inoculated culture, wherein the inoculated culture produces metapneumovirus. In one preferred embodiment, the mixed cell culture further comprises H292 cells.

The present invention provides compositions comprising a mixed cell culture comprising Calu-3 cells and a second cell type. In some preferred embodiments, the second cell type are A549 cells. In alternative embodiments, the second cell type is selected from the group consisting of RD cells, H292 cells, and BGMK cells.

Additionally, the present invention provides methods for detecting a virus, comprising: providing a mixed cell culture comprising Calu-3 cells and A549 cells, and a sample suspected of containing a virus; inoculating the mixed cell culture with the sample to produce an inoculated culture; and detecting the presence of the virus in the inoculated culture. In some preferred embodiments, the virus is a respiratory virus, which in particularly preferred embodiments is selected from but not limited to influenza A virus, influenza B virus, parainfluenza virus 2, parainfluenza virus 3, adenovirus, and respiratory syncytial virus. In other embodiments, the virus is a herpesvirus, which in particularly preferred embodiments is selected from but not limited to herpes simplex type 1, herpes simplex type 2, cytomegalovirus, varicella-zoster virus, human herpes virus 6, and human herpes virus 7. In still further embodiments, the virus is an enteric virus, which in particularly preferred embodiments is selected from but not limited to Coxsackie A virus, Coxsackie B virus, enterovirus, and echovirus. Moreover the present invention provides methods further comprising, providing a monoclonal antibody reactive with a virus selected from the group consisting of a respiratory virus, a herpes virus, and enteric virus, and wherein step c comprises using the monoclonal antibody for detecting the virus. In some preferred embodiments, the monoclonal antibody comprises a fluorescent label.

Also provided by the present invention are methods for producing a virus, comprising: providing a mixed cell culture comprising Calu-3 cells and A549 cells, and a sample suspected of containing a virus; inoculating the mixed cell culture with the sample to produce an inoculated culture; and incubating the inoculated culture under conditions suitable for producing the virus. In some preferred embodiments, the virus is a respiratory virus, which in particularly preferred embodiments is selected from but not limited to influenza A virus, influenza B virus, parainfluenza virus 2, parainfluenza virus 3, adenovirus, and respiratory syncytial virus. In other preferred embodiments, the virus is a herpesvirus, which in particularly preferred embodiments is selected from but not limited to herpes simplex type 1, herpes simplex type 2, cytomegalovirus, varicella-zoster virus, human herpes virus 6, and human herpes virus 7. In alternative embodiments, the virus is an enteric virus, which in particularly preferred embodiments is selected from but not limited to Coxsackie virus (e.g., A and/or B), enterovirus, and echovirus.

Moreover, the present invention provides kits for the detection of a virus in a sample, comprising: a mixed cell culture comprising Calu-3 cells and A549 cells; and a monoclonal antibody reactive with a virus. In some preferred embodiments, the virus is a respiratory virus, which in particularly preferred embodiments is selected from but not limited to influenza A virus, influenza B virus, parainfluenza virus 2, parainfluenza virus 3, adenovirus, and respiratory syncytial virus. In other preferred embodiments, the virus is a herpesvirus, which in particularly preferred embodiments is selected from but not limited to herpes simplex type 1, herpes simplex type 2, cytomegalovirus, varicella-zoster virus, human herpes virus 6, and human herpes virus 7. In alternative preferred embodiments, the virus is an enteric virus, which in particularly preferred embodiments is selected from but not limited to Coxsackie virus (e.g., A and/or B), enterovirus, and echovirus.

Definitions

To facilitate understanding of the invention, a number of terms are defined below.

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, sputum, and saliva, as well as solid tissue. These terms also refers to swabs and other sampling devices, which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing microorganisms may (or may not) first be subjected to an enrichment means to create a "pure culture" of microorganisms. By "enrichment means" or "enrichment treatment," the present invention contemplates (I) conventional techniques for isolating a particular microorganism of interest away from other microorganisms by means of any culture medium and/or technique, and (ii) novel techniques for isolating particular microorganisms away from other microorganisms. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "organism" and "microorganism," are used to refer to any species or type of microorganism, including but not limited to viruses and bacteria, including *rickettsia* and *chlamydia*. Thus, the term encompasses, but is not limited to DNA and RNA viruses, as well as organisms within the orders Rickettsiales and Chiamydiales.

As used herein, the term "culture," refers to any sample or specimen, which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal or insect tissue. These cultures may be derived from adults as well as fetal tissue.

As used herein, the term "finite cell lines," refer to cell cultures that are capable of a limited number of population doublings prior to senescence.

As used herein, the term "continuous cell lines," refer to cell cultures that have undergone a "crisis" phase during which a population of cells in a primary or finite cell line apparently ceases to grow, but yet a population of cells emerges with the general characteristics of a reduced cell size, higher growth rate, higher cloning efficiency, increased tumorigenicity, and a variable chromosomal complement. These cells often result from spontaneous transformation in vitro. These cells have an indefinite lifespan.

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the term "hybridomas," refers to cells produced by fusing two cell types together. Commonly used hybridomas include those created by the fusion of antibody-secreting B cells from an immunized animal, with a malignant myeloma cell line capable of indefinite growth in vitro. These cells are cloned and used to prepare monoclonal antibodies.

As used herein, the term "mixed cell culture," refers to a mixture of two types of cells. In some preferred embodiments, the cells are cell lines that are not genetically engineered, while in other preferred embodiments the cells are genetically engineered cell lines. In some embodiments, the one or more of the cell types is re "permissive" (i.e., virus is capable of replication and spread from cell to cell within the culture). The present invention encompasses any combination of cell types suitable for the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

As used therein, the term "suitable for the detection of intracellular parasites," refers to cell cultures that can be successfully used to detect the presence of an intracellular parasite in a sample. In preferred embodiments, the cell cultures are capable of maintaining their susceptibility to infection and/or support replication of the intracellular parasite. It is not intended that the present invention be limited to a particular cell type or intracellular parasite.

As used herein, the term "susceptible to infection" refers to the ability of a cell to become infected with virus or another intracellular organism. Although it encompasses "permissive" infections, it is not intended that the term be so limited, as it is intended that the term encompass circumstances in which a cell is infected, but the organism does not necessarily replicate and/or spread from the infected cell to other cells. The phrase "viral proliferation," as used herein describes the spread or passage of infectious virus from a permissive cell type to additional cells of either a permissive or susceptible character.

As used herein, the terms "monolayer," "monolayer culture," and "monolayer cell culture" refer to cells that have adhered to a substrate and grow in as a layer that is one cell in thickness. Monolayers may be grown in any format, including but not limited to flasks, tubes, coverslips (e.g., shell vials), roller bottles, etc. Cells may also be grown attached to microcarriers, including but not limited to beads.

As used herein, the term "suspension," and "suspension culture," refers to cells that survive and proliferate without being attached to a substrate. Suspension cultures are typically produced using hematopoietic cells, transformed cell lines, and cells from malignant tumors.

As used herein, the terms "culture media," and "cell culture media," refers to media that are suitable to support the growth of cells in vitro (i.e., cell cultures). It is not intended that the term be limited to any particular culture medium. For example, it is intended that the definition encompass outgrowth as well as maintenance media. Indeed, it is intended that the term encompass any culture medium suitable for the growth of the cell cultures of interest.

As used herein, the term "obligate intracellular parasite," (or "obligate intracellular organism) refers to any organism, which requires an intracellular environment for its survival and/or replication. Obligate intracellular parasites include viruses, as well as many other organisms, including certain bacteria (e.g., most members of the orders Rickettsiales [e.g., *Coxiella, Rickettsia* and *Ehrlichia*] and Chlamydiales [e.g., *C. trachomatis, C. psittaci*], etc). The term "intracellular parasite," refers to any organism that may be found within the cells of a host animal, including but not limited to obligate intracellular parasites briefly described above. For example, intracellular parasites include organisms such as *Brucella, Listeria, Mycobacterium* (e.g., *M. tuberculosis* and *M. leprae*), and *Plasmodium*, as well as *Rochalimea*.

As used herein, the term "antimicrobial," is used in reference to any compound, which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms.

As used herein, the terms "chromogenic compound," and "chromogenic substrate," refer to any compound useful in detection systems by their light absorption or emission characteristics. The term is intended to encompass any enzymatic cleavage products, (soluble, as well as insoluble), which are detectable either visually or with optical machinery. Included within the designation "chromogenic" are all enzymatic substrates, which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator," encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator," and "oxidation-reduction indicator," encompasses all compounds commonly used for detection of oxidation/reduction potentials (i.e., "eH") including, but not limited to various types or forms of tetrazolium, resazurin, and methylene blue.

As used herein, the term "inoculating suspension," or "inoculant," is used in reference to a suspension, which may be inoculated with organisms to be tested. It is not intended that the term "inoculating suspension," be limited to a particular fluid or liquid substance. For example, inoculating suspensions may be comprised of water, saline, or an aqueous solution. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "kit," is used in reference to a combination of reagents and other materials.

As used herein, the term "primary isolation," refers to the process of culturing organisms directly from a sample. As used herein, the term "isolation," refers to any cultivation of organisms, whether it be primary isolation or any subsequent cultivation, including "passage," or "transfer," of stock cultures of organisms for maintenance and/or use.

As used herein, the term "presumptive diagnosis," refers to a preliminary diagnosis, which gives some guidance to the treating physician as to the etiologic organism involved in the patient's disease. Presumptive diagnoses are often based on "presumptive identifications," which as used herein refer to the preliminary identification of a microorganism.

As used herein, the term "definitive diagnosis," is used to refer to a final diagnosis in which the etiologic agent of the patient's disease has been identified. The term "definitive identification" is used in reference to the final identification of an organism to the genus and/or species level.

The term "recombinant DNA molecule," as used herein refers to a DNA molecule, which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene," refers to a DNA sequence comprising the coding region of a gene or, in other words, the DNA sequence, which encodes a gene product. The coding region may be present in either a cDNA or genomic DNA form. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers and/or promoters, splice junctions, intervening sequences, polyadenylation signals, etc. or a combination of both endogenous and exogenous control elements.

The term "transcription unit," as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element," as used herein refers to a genetic element, which controls some aspect of the expression of nucleic acid sequences. For example, a promoter is a regulatory element, which facilitates the initiation of transcription of an operably linked coding region. Other regulatory elements are splicing signals, polyadenylation signals, termination signals, etc. (defined infra).

The terms "reporter gene construct," or "reporter gene vector," as used herein refers to a recombinant DNA molecule containing a sequence encoding the product of a reporter gene and appropriate nucleic acid sequences necessary for the expression of the operably linked coding sequence in a particular host organism. Eukaryotic cells are known to utilize promoters, enhancers, and termination and polyadenylation signals.

The term "reporter gene," refers to an oligonucleotide having a sequence encoding a gene product (typically an enzyme), which is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include but are not limited to bacterial genes encoding-galactosidase (lacZ), the bacterial chloramphenicol acetyltransferase (cat) genes, firefly luciferase genes and genes encoding-glucuronidase (GUS).

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237 [1987]). Promoter and enhancer elements have been isolated from a variety of eukaryotic sources including genes in yeast, insect and mammalian cells and viruses (analogous control elements [i.e., promoters, are also found in prokaryotes]). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 [1986], and Maniatis, et al., supra [1987]). For example, the SV40 early gene enhancer is very active in a wide variety of cell types from many mammalian species and has been widely used for the expression of proteins in mammalian cells (Dijkema, et al., EMBO J. 4:761 [1985]). Two other examples of promoter/enhancer elements active in a broad range of mammalian cell types are those from the human elongation factor 125 gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]), and the human cytomegalovirus (Boshart et al., Cell 41:521 [1985]).

The term "promoter/enhancer," denotes a segment of DNA which contains sequences capable of providing both promoter and enhancer functions (for example, the long terminal repeats of retroviruses contain both promoter and enhancer functions). The enhancer/promoter may be "endogenous," or "exogenous," or "heterologous." An endogenous enhancer/promoter is one, which is naturally linked with a given gene in the genome. An exogenous (heterologous) enhancer/promoter is one, which is placed in juxtaposition to a gene by means of genetic manipulation (i.e., molecular biological techniques).

The presence of "splicing signals," on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site," or "poly A sequence," as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7). This 237 bp fragment is contained within a 671 bp BamHI/PstI restriction fragment.

The term "genetically engineered cell line," refers to a cell line that contains heterologous DNA introduced into the cell line by means of molecular biological techniques (i.e., recombinant DNA technology).

The term "stable transfection," or "stably transfected," refers to the introduction and integration of foreign DNA into the genome of the transfected cell. The term "stable transfectant," refers to a cell, which has stably integrated foreign DNA into the genomic DNA.

The term "stable transfection" (or "stably transfected"), refers to the introduction and integration of foreign DNA into the genome of the transfected cell. The term "stable transfectant," refers to a cell, which has stably integrated foreign DNA into the genomic DNA.

The term "selectable marker," as used herein refers to the use of a gene which encodes an enzymatic activity that confers resistance to an antibiotic or drug upon the cell in which the selectable marker is expressed. Selectable markers may be "dominant"; a dominant selectable marker encodes an enzymatic activity, which can be detected in any mammalian cell line. Examples of dominant selectable markers include the bacterial aminoglycoside 3' phosphotransferase gene also referred to as the neo gene), which confers resistance to the drug G418 in mammalian cells, the bacterial hygromycin. G phosphotransferase (hyg) gene, which confers resistance to the antibiotic hygromycin and the bacterial xanthine-guanine phosphoribosyl transferase gene (also referred to as the gpt gene), which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene, which is used in conjunction with tk cell lines, the CAD gene, which is used in conjunction with CAD-deficient cells and the mammalian hypoxanthine-guanine phosphoribosyl transferase (hprt) gene, which is used in conjunction with hprt⁻ cell lines. A review of the use of selectable markers in mammalian cell lines is provided in Sambrook et al., supra at pp. 16.9-16.15.

The terms "nucleic acid molecule encoding," "DNA sequence encoding," and "DNA encoding," refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The terms "confluent" or "confluency" as used herein in reference to an adherent cell line define a condition wherein cells throughout a culture are in contact with each other creating what appears to be a continuous sheet or "monolayer" of cells.

The terms "cytopathic effect" or "CPE" as used herein describe changes in cellular structure (i.e., a pathologic effect) resulting from external agents such viruses. Common cytopathic effects include cell destruction, syncytia (i.e., fused giant cells) formation, cell rounding vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the focus is initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. Cytopathic effects are readily discernable and distinguishable by those skilled in the art.

The abbreviation "ONPG," represents o-Nitrophenyl-D-Galactopyranoside. ONPG is a substrate for the enzyme-galactosidase (-gal). The reaction between ONPG and -gal produces a yellow product, which can be quantified spectrophotometrically at 405 nm.

The abbreviation "X-gal," represents the chemical compound 5-bromo-4-chloro-3-indolyl-D-galactopyranoside, a substrate for the enzyme-galactosidase. The reaction between X-gal and β-galactosidase results in the formation of a blue precipitate, which is visually discernable.

The term "hybriwix," represents a product of Diagnostic Hybrids, Inc., Athens, Ohio, which allows for quantification of certain viral DNA in an infected monolayer of cells by DNA hybridization. "DNA hybridization" is the annealing of two complementary DNA molecules whose base sequences match according to the rules of base pairing. DNA hybridization is used to identify or quantify an unknown or "target" DNA by hybridization to a known DNA or "probe." The probe is typically labeled with a reporter molecule such as $^{125}$I, a radioisotope, which can be detected and quantified with a gamma counter.

The phrase "plaque reduction assay," or "PRA," as used herein describes a standard method used to determine efficacy of anti-viral drugs by enumerating a decrease in plaque formation in a cell monolayer exposed to a drug. A "plaque" is a defined area of "CPE." It is usually the result of infection of the cell monolayer with a single infectious virus, which then replicates and spreads to adjacent cells of the monolayer. A plaque may also be referred to as a "focus of viral infection."

The term "permissive" as used herein describes the sequence of interactive events between a virus and its putative host cell. The process begins with viral adsorption to the host cell surface and ends with release of infectious virions. A cell is "permissive" if it readily permits the spread of virus to other cells. Many methods are available for the determination of the permissiveness of a given cell line, including, but not limited to plaque reduction assays, comparisons of the production and/or quantitation of viral proteins based on results obtained from gel electrophoresis, relative comparisons using hybridization analysis to analyze DNA or RNA content, etc.

The term "susceptible," as used herein describes the extent that a permissive or non-permissive host cell can adsorb and be penetrated by a virus. A cell line may be susceptible without being permissive in that it can be penetrated but not release virions. A permissive cell line however must be susceptible.

The phrase "seed on," as used herein describes the act of transferring an aqueous solution of suspended cells into a vessel containing cells adhered to a surface, after which the vessel is stored for a sufficient period of time to allow the suspended cells or "seeds" to settle out by gravity and attach in a relatively uniform manner to the adhered cells and become integrated into the final cell monolayer as a mixture. A "mixed cell monolayer," results from the "seed on" process.

The phrase "seed in," as used herein describes the mixing of two or more aqueous solutions of suspended tissue culture cells, each cell suspension having different cellular properties, and transfer of such mixture of cells into a vessel which is stored for a sufficient period of time to allow the suspended cells to settle out by gravity and attach in a relatively uniform manner such that the distribution of any single cell type is indicative of the relative ratio of the cells in the original mixture.

The term "starts," as used herein refers to the reporter cells, which represent a primary infection of virus. The virus infects a reporter cell (a genetically engineered cell) and induces the expression of the reporter gene. A reporter cell can be non-permissive (i.e. permissiveness of the reporter cells is not required) and still produce starts.

As used herein, the term "respiratory virus" refers to a virus that infects a cell of the respiratory tract (air passages from the nose to the pulmonary alveoli, through the pharynx, larynx, trachea, and bronchi). Exemplary "respiratory viruses" include but are not limited to influenza viruses, parainfluenza viruses, respiratory syncytial viruses (RSV), adenoviruses, rhinoviruses, and severe acute respiratory syndrome (SARS) viruses.

As used herein, the terms "herpes virus" and "herpesvirus" refers to a virus belonging to the Herpesviridae family of large, enveloped double-stranded DNA virus. Exemplary "herpesviruses" include but are not limited to Herpes simplex viruses (HSV-1 and HSV-2), varicella zoster viruses (VSV), Epstein Barr viruses (EBV), and cytomegaloviruses (CMV).

As used herein, the term "enteric virus" refers to a virus that infects a cell of the gastrointestinal tract (digestive tract extending from the cavity, through the esophagus, stomach, duodenum, small intestine, large intestine, rectum and anus). Exemplary enteric viruses include but are not limited to coxsackieviruses (type A and B), echoviruses, enteroviruses 68-71, and polioviruses.

DESCRIPTION OF THE INVENTION

The present invention generally relates to the field of diagnostic microbiology, and more particularly, to compositions and methods for detecting and differentiating one or more viruses or other intracellular parasites present in a specimen. The present invention also provides compositions and methods to evaluate the susceptibility of organisms to antimicrobial agents.

The present invention provides methods and compositions for the detection of several different viruses, as well as other intracellular organisms present in clinical and other specimens, in a single cell culture unit comprised of a mixture of cells. The mixture of cells is grown in a manner to co-exist as a monolayer of relatively equivalent ratio and demonstrating complementary susceptibilities to a wider range of viruses and/or other organisms than could be detected by each individual cell line. For example, the viral assays involve inoculating a cell mixture with a specimen suspected of containing a virus, allowing a sufficient period of time for the virus infectious cycle to proceed, followed by the detection and/or quantification of the number of virus-infected cells to determine the number of infectious virions in the specimen. This detection step may be accomplished using any number of available confirmation methods, including specific viral antigen detection using antigen-specific antibodies, nucleic acid probes, and reporter gene detection. The assay also provides reliable methods and compositions for the quantification of the number of infectious virions present in a sample. In addition, the methods and compositions of the present invention are sufficiently sensitive that the presence of a single virion in a specimen may be detected.

The present invention also provides compositions comprising novel mixtures of various cell types traditionally used in single cell assays. In preferred embodiments, the cells are mixed to produce mixed monolayer cell cultures. One such mixed cell culture includes mink lung (e.g., Mv1Lu) cells co-cultivated with human mucoepidermoid cells (e.g., NCI-H292; also referred to as "H292" cells). This cell mixture is susceptible to viruses such as influenza A, influenza B, RSV, parainfluenza types 1, 2, and 3, adenovirus, and CMV (i.e., the group of viruses most commonly associated with respiratory virus disease). In other mixed cultures, buffalo green monkey kidney cells (BGMK) are co-cultivated with NCI-H292 cells for the detection and identification of enteroviruses, such as poliovirus, echoviruses and Coxsackie virus (e.g., Coxsackie A and B viruses), and numbered EV strains. In addition to enteroviruses, it is contemplated that the present invention encompasses cell types that are susceptible to picornaviruses such as Hepatitis A.

The present invention also provides compositions comprising novel mixtures of different cell types traditionally used in single cell assays that are co-cultivated with genetically engineered cells. In particularly preferred embodiments, the genetically engineered cell line is a DNA-transfected cell line that is susceptible to infection by a virus, the cell line having been stably transformed with a chimeric gene comprising a virus-inducible promoter and a gene coding for an enzyme, the expression of the enzyme being dependent upon the presence of the virus. Such genetically engineered cells are described, for example, in U.S. Pat. No. 5,418,132, herein incorporated by reference. In one preferred embodiment, a cell mixture includes human lung fibroblasts (e.g., MRC-5 cells) co-cultivated with a stable baby hamster kidney (BHK) cell line, the genome of which has been engineered to contain the *E. coli* lacZ gene behind (i.e., 3' to) an inducible HSV promoter, HSV-1 ICP6 promoter (BHK/ICP6LacZ-5 cells are available from the ATCC as CRL-12072). This cell mixture is susceptible to infection by CMV and HSV types 1 and 2.

In yet another embodiment, the present invention provides compositions comprising novel mixtures of different types of genetically engineered cells. In particularly preferred embodiments, the genetically engineered cell line is a DNA-transfected cell line that is susceptible to infection by a virus, the cell line having been stably transformed with a chimeric gene comprising a virus-inducible promoter and a gene coding for an enzyme, the expression of the enzyme being dependent upon the presence of the virus. The second genetically engineered cell line is a DNA-transfected cell line susceptible to viral infection and stably transformed with a chimeric gene comprising a virus-inducible promoter and a gene encoding a second enzyme (i.e., an enzyme that is different from that associated with the first cell line) whose expression is dependent upon the presence of a second virus. In one preferred embodiment, a cell mixture is prepared in which engineered BHK cells (e.g., BHK/ICP6/LacZ-5 cells) are co-cultivated with a stable mink lung cell line (Mv1Lu), the genome of which has been engineered to contain an inducible CMV promoter (the CMV UL45 promoter). These cells are referred to as "MLID5" cells and are disclosed in U.S. patent application Ser. No. 08/846,026, herein incorporated by reference. This cell mixture is susceptible to infection by CMV and HSV virus types 1 and 2 (HSV-1 and HSV-2), with CMV infecting the genetically engineered BHK cells, and HSV-1 and HSV-2 preferentially infecting the mink lung cells. In another embodiment, the present invention contemplates the use of genetically engineered cells (e.g., mink lung cells) in which the cell genome is engineered to contain the firefly luciferase gene behind (i.e., 3' to) an inducible CMV promoter; these cells are also described in U.S. patent application Ser. No. 08/846,026. However, it is not intended that the present invention be limited to any particular cell types or cell lines, nor is it intended that the present invention be limited to any particular combinations of cells. It is also not intended that the present invention be limited in terms of the genetically engineered cells.

The following Table provides a matrix indicating the ability of various cells to form single, confluent monolayers, as well as co-cultivated confluent, mixed cell monolayers.

In yet another embodiment, the present invention provides kits for assaying samples for the presence of infectious viruses. In these kits, mixed cell cultures are provided which facilitate the detection and identification of particular virus groups (e.g., viruses associated with respiratory infections/diseases). In the kits, co-cultivated cells are supplied either frozen or dispensed (i.e., ready for use) in shell vials, tubes, or multiwell plates. These cells are susceptible to infection by the virus group of interest as indicated by the sample type. In preferred embodiments, the kits also include reagents necessary to detect expression of viral antigens or virus-induced reporter gene expression.

One of the several advantages of the present invention is that it provides rapid and sensitive assay systems for the detection and identification of a single virus type from a multiplicity of possibilities, in a single mixed cell unit that is suitable for diagnostic assay. Thus, the present invention: eliminates the need for multiple cell lines cultured in individual containers; provides reliable results in 1-3 days following inoculation of the cell cultures (rather than 1-28 days); eliminates the necessity of working with primary cell cultures; provides an efficient screening method for grouping and preliminary identification of viruses; and provides assay systems that are highly specific for viruses capable of inducing reporter gene expression. Thus, the present invention clearly fulfills a need that has been heretofore unmet in the field of diagnostic virology.

In a further embodiment, the invention provides a composition comprising a mixed cell culture comprising MDCK cells and one or more of A549 cells and H292 cells. These compositions are useful in detecting the presence of one or more of influenza viruses (such as influenza A and/or B), respiratory syncytial virus (RSV), adenovirus, parainfluenza 1 virus, parainfluenza 2 virus, parainfluenza 3 virus, and metapneumovirus. These methods are also useful in producing one or more of influenza viruses (such as influenza A and/or B), respiratory syncytial virus (RSV), adenovirus, parainfluenza 1 virus, parainfluenza 2 virus, parainfluenza 3 virus, and metapneumovirus.

The term "MDCK cells" and "Madin-Darby canine kidney cells" refer to cells that were isolated as previously described (Madin & Darby (1958) Tech. Prog. Rep. No. 25, Appendix VIII, p. 276. Naval Biological Laboratory, California, and to cells that are established from these cells. MDCK cells are exemplified, but not limited to those deposited as ATCC accession number CCL-34. The term

TABLE 1

| Cell Cultures | | | | | | | | | |
|---|---|---|---|---|---|---|---|---|---|
| | MRC-5 1 | CV-1 2 | BGMK 3 | McCoy 4 | BHK* 5 | A549 6 | HEp-2 7 | Mv1Lu 8 | NCI-H292 9 |
| MRC-5 A | ++ | + | No | + | + | + | + | + | + |
| CV-1 B | | ++ | No | + | + | + | + | + | + |
| BGMK C | | | ++ | + | + | + | + | + | + |
| McCoy D | | | | ++ | + | + | Yes | + | + |
| BHK* E | | | | | ++ | + | + | + | + |
| A549 F | | | | | | ++ | + | + | + |
| HEp-2 G | | | | | | | ++ | + | + |
| Mv1Lu H | | | | | | | | ++ | + |
| NCI-H292 I | | | | | | | | | ++ |

++ Denotes single cell types producing confluent monolayers
+ Denotes some degree of dimorphic, mixed monolayer
Yes Denotes cell mixtures that appear very uniform, with an even distribution
No Denotes cell mixtures that did not appear to work
*Denotes genetically engineered ELVIS BHK cells.

"established from" when made in reference to any cell disclosed herein (such as MDCK cell, A549 cell, H292 cell, etc.), refers to a cell that has been obtained (e.g., isolated, purified, etc.) from the parent cell using any manipulation. Suitable manipulations include without limitation, infection with virus, transfection with DNA sequences, treatment and/or mutagenesis using for example chemicals, radiation, etc., and selection (such as by serial culture) of any cell that is contained in cultured parent cells. For example, the invention includes within its scope cell lines that may be established from any cell disclosed herein (such as MDCK cell, A549 cell, H292 cell, etc.) by treatment with chemical compounds and electromagnetic radiation. Suitable chemical compounds include but are not limited to N-ethyl-N-nitrosourea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6 MP), mitomycin-C (MMC), procarbazine (PRC), N-methyl-N'-nitro-N-nitrosoguanidine (MNNG), $^3H_2O$, and urethane (UR). Electromagnetic radiation encompasses for instance X-ray radiation, gamma-radiation, and ultraviolet light.

Thus, reference to any virus or cell herein includes "wild-type" viruses and cells (i.e., a virus or cell whose genome has not been manipulated by man) and "transgenic" viruses and cells (i.e., a virus or cell that contains a heterologous nucleic acid sequence introduced into the virus or cell by means of molecular biological techniques). Transgenic viruses and cells may contain heterologous nucleotide sequences; such as reporter genes (such as e.g., the uid A gene, β-glucuronidase gene, green fluorescent protein gene, *E. coli* β-galactosidase (LacZ) gene, *Halobacterium* β-galactosidase gene, *E. coli* luciferase gene, *Neuropsora* tyrosinase gene, Aequorin (jellyfish bioluminescence) gene, human placental alkaline phosphatase gene, and chloramphenicol acetyltransferase (CAT) gene); transcriptional and translational regulatory sequences; selectable marker proteins (e.g., proteins that confer drug resistance such as the bacterial aminoglycoside 3' phosphotransferase gene (also referred to as the neo gene), which confers resistance to the drug G418 in cells; the bacterial hygromycin G phosphotransferase (hyg) gene, which confers resistance to the antibiotic hygromycin; and the bacterial xanthine-guanine phosphoribosyl transferase gene (also referred to as the gpt gene), which confers the ability to grow in the presence of mycophenolic acid; the HSV-tk gene and the dt gene); probe genes (such as the staphylococcal protein A and its derivative ZZ, which binds to human polyclonal IgG; histidine tails, which bind to $Ni^{2+}$; biotin, which binds to streptavidin; maltose-binding protein (MBP), which binds to amylase; and glutathione S-transferase, which binds to glutathione); and receptor genes.

In one embodiment, equivalent cells within the scope of the invention include cells that are established from the exemplary MDCK cells deposited as ATCC accession CCL-34, and that have substantially the same sensitivity, increased sensitivity, or reduced sensitivity to one or more of influenza virus A and influenza virus B as the cell from which it is established. The term "sensitivity" and "sensitive" when made in reference to a cell is a relative term, which refers to the degree of permissiveness of the cell to a virus as compared to the degree of permissiveness of another cell to the same virus. For example, the term "increased sensitivity" to influenza virus, when used in reference to the sensitivity of a first cell relative to a second cell, refers to an increase in the quantity of influenza virus (e.g., protein, nucleic acid, and/or CPE) obtained from progeny virus produced following influenza virus infection of a first cell, as compared to the quantity of influenza virus (e.g., protein, influenza virus nucleic acid, and/or CPE) obtained from progeny virus produced following influenza virus infection of a second cell. In some embodiments, the increase is preferably at least a 5%, more preferably from 5% to 10,000%, more preferably from 5% to 1,000%, yet more preferably from 10% to 200%, and even more preferably from 10% to 100%. For example, if 34 samples containing influenza virus were tested for the presence of progeny virus, with 25 and 13 samples showing the presence of CPE using a first cell and second cell, respectively, then the sensitivity is 74% and 38% for the first cell and second cell, respectively. This reflects an increase of 90% in the sensitivity of the first cell as compared to the sensitivity of the second cell.

In another embodiment, equivalent cells within the scope of the invention include cells that are established from the exemplary MDCK deposited as ATCC accession number CCL-34, and that have substantially the same sensitivity to influenza virus as the cell from which it is established. This may be advantageous where, for example, the parent cell is made transgenic for a reporter gene.

In a further embodiment, equivalent cells within the scope of the invention include cells that are established from the exemplary MDCK deposited as ATCC accession number CCL-34, and that have increased sensitivity or decreased sensitivity to influenza virus as compared to cells from which they were established. This may be desirable where, for example, the parent cell is made transgenic for a receptor gene, which alters the level of binding of influenza B virus to the cell.

The invention's methods that employ mixed cell cultures containing MDCK cells are useful for detecting influenza virus. The term "detecting" when in reference to detecting the presence of any virus in cells refers to determining the presence, using any method, of the virus inside the cells, on the cells, and/or in the medium with which the cells come into contact. These methods are exemplified by, but not limited to, the observation of cytopathic effect, detection of viral protein, such as by immunofluorescence and Northern blots, and detection of viral nucleic acid sequences, such as by PCR, reverse transcriptase PCR (RT-PCR), Southern blots and Northern blots.

As used herein the term "influenza virus" refers to members of the orthomyxoviridae family of enveloped viruses with a segmented antisense RNA genome (Knipe and Howley (eds.) *Fields Virology*, 4th edition, Lippincott Williams and Wilkins, Philadelphia, Pa. [2001]). Two types of influenza virus (A and B) are human pathogens causing respiratory pathology.

When A549 and/or H292 cells are in mixed cell culture with MDCK cells, the mixed cell cultures may also be used to detect and propagate other viruses than influenza virus, such as respiratory syncytial virus (RSV), adenovirus, parainfluenza 1 virus, parainfluenza 2 virus, parainfluenza 3 virus, and metapneumovirus.

The terms "respiratory syncytial virus" and "RSV" refer to one or more members of the family Paramyxoviridae, subfamily pneumovirus, which are enveloped, single stranded antisense RNA viruses that infect the respiratory tract (Schmidt and Emmons (eds.) Diagnostic Procedures for Viral, Rickettsial and Chlamydial Infections, 6th edition, American Public Health Assoc. Inc., Washington, D.C. [1989]), There are two major strains of RSV represented by, but not limited to, Long (Group 1) ATCC VR-26, and 18537

(Group 2) ATCC VR-1401. The following five exemplary human RSV strains are available from ATCC: VR-1400, VR-1401, VR-1540, VR-26, and VR-955.

As used herein, the term "parainfluenza virus" refers to certain members of the paramyxoviridae family of enveloped viruses with a single-stranded antisense RNA genome (Knipe and Howley (eds.) *Fields Virology*, 4th edition, Lippincott Williams and Wilkins, Philadelphia, Pa. [2001]). Four types of parainfluenza virus (1 to 4) are human respiratory pathogens. Prototype strains of the human paramyxoviruses parainfluenza types 1, 2, 3, 4A, 4B, and mumps, may be obtained from the reference virus collection of the Respiratory and Enteric Viruses Branch of the Center for Infectious Diseases, Centers for Disease Control ("CDC"), Atlanta, Ga. (see U.S. Pat. No. 5,262,359 to Hierholzer). These strains are also available from the ATCC, Rockville, Md., under accession numbers VR-94, VR-92, VR-93, VR-279, VR-579, and VR-106, respectively (see U.S. Pat. No. 5,262,359 to Hierholzer).

As used herein, the term "adenovirus" refers to a double-stranded DNA adenovirus of animal origin, such as avian, bovine, ovine, murine, porcine, canine, simian, and human origin. Avian adenoviruses are exemplified by serotypes 1 to 10, which are available from the ATCC, such as, for example, the Phelps (ATCC VR-432), Fontes (ATCC VR-280), P7-A (ATCC VR-827), IBH-2A (ATCC VR-828), J2-A (ATCC VR-829), T8-A (ATCC VR-830), and K-11 (ATCC VR-921) strains, or else the strains designated as ATCC VR-831 to 835. Bovine adenoviruses are illustrated by those available from the ATCC (types 1 to 8) under reference numbers ATCC VR-313, 314, 639-642, 768 and 769. Ovine adenoviruses include the type 5 (ATCC VR-1343) or type 6 (ATCC VR-1340). Murine adenoviruses are exemplified by FL (ATCC VR-550) and E20308 (ATCC VR-528). Porcine adenovirus (5359) may also be used. Adenoviruses of canine origin include all the strains of the CAVI and CAV2 adenoviruses [for example, Manhattan strain or A26/61 (ATCC VR-800) strain]. Simian adenoviruses are also contemplated, and they include the adenoviruses with the ATCC reference numbers VR-591-594, 941-943, and 195-203. Human adenoviruses, of which there greater than fifty (50) serotypes are known in the art, are also contemplated, including the Ad2, Ad3, Ad4, Ad5, Ad7, Ad9, Ad12, Ad17, and Ad40 adenoviruses.

The terms "metapneumovirus" and "MPV" refer to a negative-sense single stranded RNA virus belonging to the Paramyxoviridae family, subfamily Pneumovirinae, and genus Metapneumovirus. MPV includes mammalian MPV, which is exemplified by human, primate, horse, cow, sheep, pig, goat, dog, cat, avian and rodents MPV. Mammalian MPV is phylogenetically more closely related to particular virus isolates than to turkey rhinotracheitis virus, the etiological agent of avian rhinotracheitis, and is identified by its genomic organization (see, for example, U.S. patent application publication numbers 20030232326, 20040005544, 20040005545, and 20030232061, and published WO 02057302A2 and WO 03072719A2). The invention contemplates each of the variant MPV that are idnetified based on the relative homology of their genomic sequences to other viruses, as described in, for example, U.S. patent application publication numbers 20030232326, 20040005544, 20040005545, and 20030232061, and published WO 02057302A2 and WO 03072719A2.

MPV may be detected by, for example: detecting cytopathic effect in the exemplary LLC-MK2 cells and HEp-2 cells (Chan et al. 2003 Emerging Infectious Diseases, 9:1058-1063; Setterquist et al., 19$^{th}$ Annual Clinical Virology Symposium, Clearwater Fla., Apr. 27-30, 2003); detecting MPV proteins using antibodies; and/or detecting MPV nucleic acid sequences (see, for example, U.S. patent application publication numbers 20030232326 and 20040005544). In one embodiment, MPV nucleic acid sequences may be detected in the absence of detectable CPE.

The invention's data is the first demonstration of the use of MDCK in mixed cell culture (Examples 4-9), and is contrasted with Frank et al. (1979) Journal of Clinical Microbiology, 10(1):32-36 which disclosed using MDCK cells. The ability to grow MDCK in mixed cell culture with the exemplary cell lines of H292 and A549 was surprising in view of data herein (Example 1) which demonstrates the unpredictability of co-culturing two or more cell lines, as well as the unpredictability that once co-cultured, the cells will retain their biological activity in detecting and/or producing virus.

One advantage of using MDCK cells in the invention's mixed cell cultures with A549 and/or H292 is that these cells are non-permissive to SARS-CoV infection as determined by CPE (Table 12 herein; see also Drosten, et al., 2003, N. Engl. J. Med. 348:1967-1976; Ksiazek, et al., 2003, N. Engl. J. Med. 348:1953-1966; Peiris, et al., 2003, Lancet 361: 1319-1325). Thus, an advantage of using MDCK cells is that they permit detection of respiratory viruses (such as respiratory syncytial virus (RSV), adenovirus, parainfluenza 1 virus, parainfluenza 2 virus, parainfluenza 3 virus, and metapneumovims), while being nonpermissive, or having a low level of permissivity, to SARS-CoV (Table 12). Thus, mixed cell cultures containing MDCK are useful for increasing the safety of cell cultures that are used in screening clinical samples for respiratory pathogens other than SARS-coronavirus. This is particularly useful in small laboratories that detect respiratory viruses (such as respiratory syncytial virus (RSV), adenovirus, parainfluenza 1 virus, parainfluenza 2 virus, and parainfluenza 3 virus), because the use of mixed cell cultures containing MDCK by these laboratories would obviate the need to resort to containment approaches that would otherwise be required for cells producing infectious SARS-CoV.

In particular, although both MDCK and Mv1Lu cells are susceptible to influenza B virus (Example 2), data herein shows, surprisingly, that MDCK has a substantially lower level of permissivity and/or susceptibility to SARS-CoV as compared to Mv1Lu (Table 12). The terms "lower," "smaller," "reduced," "decreased" and grammatical equivalents, when used in reference to the level of permissivity and/or susceptibility to a virus of a first cell type relative to a second cell type, mean that the level of permissivity and/or susceptibility of a first cell type is lower than that of a second cell type. In preferred embodiments, the difference in permissivity and/or susceptibility is statistically significant, using any art-accepted statistical method of analysis. In one embodiment, the level of permissivity and/or susceptibility to the virus of the first sample is at least 10% lower than the level of permissivity and/or susceptibility of the second cell type. In some embodiments, the level of permissivity and/or susceptibility is at least 25% lower than, at least 50% lower than, at least 75% lower than, at least 85% lower than, at least 90% lower than, at least 95% lower than, and/or at least 99% lower than that of the second cell type. Data herein shows that, in one embodiment, the level of permissivity and/or susceptibility of MDCK cells to SARS-CoV is 0.004% the level of susceptibility of Mv1Lu cells (Table 12).

The terms "SARS coronavirus," "SARS-CoV," and "severe acute respiratory syndrome coronavirus" are equivalent, and are used to refer to an RNA virus that is the causative agent of severe acute respiratory syndrome (Drosten, et al., 2003, supra; Fouchier, et al., 2003, supra; Ksiazek, et al., 2003, supra; Peiris, et al., 2003, supra; Poutanen, et al., 2003, supra). Exemplary strains of SARS coronavirus include, but are not limited to, Urbani, Tor2, CUHK-W1, Shanhgai LY, Shanghai QXC, ZJ-HZ01, TW1, HSR 1, WHU, TWY, TWS, TWK, TWJ, TWH, HKU-39849, FRA, TWC3, TWC2, TWC, ZMY 1, BJ03, ZJ01, CUHK-Su10, GZ50, SZ16, SZ3, CUHK-W1, Bj04, AS, Sin2774, GD01, Sin2500, Sin2677, Sin2679, Sin2748, ZJ-HZ01, and BJ01.

However, coronaviruses can establish persistent infection in cells without inducing CPE, suggesting that CPE may not be an accurate indicator of infection (Chaloner, et al., 1981, Arch. Virol. 69:117-129). Data herein confirmed this surprising observation by demonstrating replication of SARS-CoV in the absence of CPE. For example, Example 12 shows replication of SARS-CoV, as detected by sgRNA and virus titers, in the absence of CPE. In particular, significant CPE was not observed in pRhMK, pCMK, R-mix (Mv1Lu and A549), Mv1Lu, HEK-293T, and Huh-7 cells at 5 days post infection, although virus titers as well as SARS-CoV sgRNA were actually increased within 24 hours post infection (Table 12).

The terms “subgenomic RNA” and “sgRNA” are used interchangeably herein to refer to a nucleotide sequence comprising at least a portion of the leader sequence of SARS-CoV.

The term “leader sequence” refers to a sequence of about 40 to about 150, about 50 to about 80, and or about 55 to about 75, nucleotides that is located at the 5' terminus of the genome. This sequence is juxtaposed to the 5' terminus of each subgenomic RNA by transcriptional mechanisms during synthesis. There is very strong sequence conservation of the leader sequence across the strains of SARS. In one embodiment, the leader sequence is exemplified by the sequence from nucleotide 1 to nucleotide 72 for SARS-CoV (Urbani) 5'-atattaggtttttacctacccaggaaaagccaaccaacctcgatctcttgtagatctgttctctaaacgaac-3' (SEQ ID NO:1); 5'-tattaggtttttacctacccaggaaaagccaaccaacctcgatctcttgtagatctgttctctaaacgaac-3' (SEQ ID NO:2) of gi|33304219|gb|AY351680.1| SARS coronavirus ZMY 1,5'-taggttttacctacccaggaaaagccaaccaacctcgatctctgtagatctgttctctaaacgaac-3' (SEQ ID NO:3) of gi|31416305|gb|AY278490.3| SARS coronavirus BJ03, 5'-ctacccaggaaaagccaaccaacctcgatctcttgtagatctgttctctaaacgaac-3' (SEQ ID NO:4) of gi|30421451|gb|AY282752.1| SARS coronavirus CUHK-su10, tacccaggaaaagccaaccaacctcgatctcettgtagatctgttactaaacgaac-3' (SEQ ID NO:5) of gi|31416306|gb|AY279354.2| SARS coronavirus BJ04, and 5'-ccaggaaaagccaaccaacctcgatctcttgtagatctgttctctaaacgaac-3' (SEQ ID NO:6) of gi|30275666|gb|AY278488.2| SARS coronavirus BJ01.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); M (micromolar); N (Normal); mol (moles); mmol (millimoles); mol (micromoles); mmol (nanomoles); g (grams); mg (milligrams); g (micrograms); ng (nanograms); l or L (liters); ml (milliliters); l (microliters); cm (centimeters); mm (millimeters); m (micrometers); nm (nanometers); ×g (times gravity); ° C. (degrees Centigrade); FBS (fetal bovine serum); PBS (phosphate buffered saline; HEPES (N-[2-hydroxyethyl]piperazine-N'-[2-ethanesulfonic acid]); HBSS (Hank’s Balanced Salt Solution); MEM (Minimal Essential Medium); EMEM (Eagle’s Minimal Essential Medium); BBL (Becton Dickinson Microbiology Systems, Cockeysville, Md.); DIFCO (Difco Laboratories, Detroit, Mich.); U.S. Biochemical (U.S. Biochemical Corp., Cleveland, Ohio); Chemicon (Chemicon, Inc., Temecula, Calif.); Dako (Dako Corporation, Carpinteria, Calif.); Fisher (Fisher Scientific, Pittsburgh, Pa.); Sigma (Sigma Chemical Co., St. Louis, Mo.); ATCC (American Type Culture Collection, Rockville, Md.); Bartel’s (Bartels, Issaquah, Wash.); and BioWhittaker (BioWhittaker, Walkersville, Md.).

The cells used during the development of the present invention and described in the following Examples, were obtained from the ATCC, with the exception of BGMK and PRMK cells obtained from BioWhittaker, and MRC-5 cells obtained from both ATCC and BioWhittaker. The ATCC numbers of the cells are indicated in the following Table.

TABLE 2

ATCC Cell Lines

| Cell Line | ATCC Number |
|---|---|
| BHK/ICP6LacZ-5 | CCL-12072 |
| A549 | CCL-185 |
| CV-1 | CCL-70 |
| HEp-2 | CCL-23 |
| hs27 | CRL-1634 |
| Mv1Lu | CCL-64 |
| McCoy | CCL-1696 |
| NCI-H292 | CCL-1848 |
| MRC-5 | CCL-171 |
| WI-38 | CCL-75 |
| Vero | CCL-81 |
| MDCK (NBL-2) | CCL-34 |
| BHK21 | CCL-10 |
| HEL299 | CCL-137 |
| HeLa | CCL-2 |
| Mv1Lu-hF | PTA-4737 |

Example 1

Co-Cultivation of Cells

In this Example, mixed cell cultures were established in which single, dimorphic cell sheets were produced at confluency.

In these experiments, all of the cell lines were cultured to confluency in sterile polystyrene flasks in EMEM (Eagle’s Minimal Essential Medium) with 25 mM HEPES, 7% fetal bovine serum (FBS), 2 mM L-glutamine, and penicillin/streptomycin (100 Units/100 g per ml of medium each).

Cells to be cultured were harvested by first rinsing source cell monolayers with Hank’s Balanced Salt Solution (HESS) without magnesium or calcium. Depending upon the cell line, the cells were dissociated by adding trypsin (0.125% in HESS, without calcium or magnesium) or trypsin-EDTA (0.25% in 1 mM EDTA in HESS, without calcium or magnesium), or directly to the cell monolayer, and incubating for approximately 5 minutes at ambient temperature. Ten volumes of cell culture medium was added to each trypsinized cell suspension and the cells were repeatedly pipetted in order to produce near-single cell suspensions (i.e., without cell aggregates). Each trypsinized cell suspension was diluted in an adequate volume of culture medium to produce an optical density of cell suspension suitable to produce a confluent monolayer of cells within 2-3 days of incubation in a 96-well microtiter plate. For single cell monolayers (i.e., one cell type per well), 0.2 ml of suspension was used to inoculate each well. For example, the final cell preparations ranged from a final optical density at 500 nm of 0.012 OD units/ml for CV-1 cells to 0.03 OD units/ml for HEp-2 cells.

Cell mixture monolayers were produced by co-planting two distinct cell types at an equal volume of each diluted cell suspension (i.e., 0.1 ml of each cell type was used to inoculate each well of a 96-well microtiter plate). The cells were allowed to attach to the well surface by gravity for 30-60 minutes, and the inoculated microtiter plates were incubated for up to three days at 36° C. in 5% $CO_2$ with 95% relative humidity.

Periodically during incubation, single and mixed monolayers were checked for overall viability. The mixed cell culture monolayers were also checked for the ability of the cell lines to co-exist and develop as a single cell sheet (i.e., a single monolayer), with two distinct cell morphologies (i.e., dimorphic cell sheets), at an approximately equal density of each cell type. At confluency, the cells were treated with a methylene blue staining solution to fix the cells and stain them a light blue in order to provide contrast for visualization using light microscopy.

Some of the mixed monolayers successfully grew as a mixed cell monolayer adhered to the well surfaces, exhibiting a smooth, evenly distributed monolayer. These mixed cultures were designated as "morphologic category 1." In these cultures, each cell type could be easily distinguished and appeared to survive well in a mixed monolayer, giving the appearance of a single cell distribution. Mixed monolayers composed of HEp-2 and McCoy cells displayed this morphology.

Some of the mixed monolayers successfully grew as a mixed monolayer adhered to the well surfaces, but exhibited two distinct morphologies at confluency. These mixed cultures were designated as "morphologic category 2." In these cultures, separate, distinct patches of each cell line co-existed within the monolayer, giving the appearance of oil mixing with water. Although an understanding of the mechanism is not necessary in order to use the present invention, it is likely that this appearance is most likely the result of contact inhibition between two specific cell types. The relative sizes of the patches were found primarily to be a function of how evenly the cells were distributed at cell planting. The more even the cell distribution at planting, the patches or islands were smaller as the monolayer reached confluency. Examples of monolayers that produced this appearance were mink lung cells co-cultivated with NCI-H292 cells, mink lung cells co-cultivated by buffalo green monkey kidney (BGMK) cells, and human lung carcinoma A549 cells co-cultivated with NCI-H292 cells.

However, some cells types could not produce a mixed cell monolayer, when mixed at relatively equal cell numbers at planting in the same culture medium. In some of these cultures, only one of the cell types was found to be viable (i.e., the culture was effectively a single cell type). Examples of mixed cell cultures that were found to be unsuitable for the production of mixed monolayers include human embryonic lung fibroblasts (MRC-5 cells) co-cultivated with BGMK cells. In this mixture, the MRC-5 cells become toxic and form aggregates of dead cells soon after planting. Thus, at confluency, the monolayer only contains one functional, viable cell type, the BGMK cells. Thus, this cell mixture was found to be unsuitable for producing mixed cell monolayers as the cells failed to form mixed cell monolayers of either a smooth or dimorphic morphologic type.

Example 2

Detection of Respiratory Viruses in Mixed Cell Cultures

In this Example, mixed cell cultures were used to detect various respiratory viruses including Influenza A, RSV, adenoviruses, parainfluenza viruses, and Influenza B, present in clinical specimens. The mixed cells used in these experiments were Mv1Lu (mink lung cells) and NCI-H292 (human mucoepidermoid cells).

Cell Lines

Confluent T-225 flasks of Mv1Lu and H292 cells were prepared in EMEM with HEPES, 10% FBS, 2 mM L-glutamine, and 50 µg/ml gentamicin. The cells were harvested by first rinsing them in 30 ml MSS without magnesium and calcium. The cells were then dissociated from the flask by brief exposure (i.e., until the cells lifted from the bottom of the flask) to 7 ml trypsin-EDTA solution as described in Example 1. Then, 30 ml media was added to the cells to prepare a cell suspension concentrate. The optical density of each cell suspension was determined at 500 nm, using 3 ml of cells. Typically, the OD reading was 0.2/ml for both the Mv1Lu and H292 cells. In addition to the Mv1Lu and H292 cells, rhesus monkey kidney cells (PRMK), A549 cells, and MDCK cells were used in the present Example. These additional cell lines were prepared in single cell cultures as known in the art.

Mixed Cell Cultures

When each cell suspension concentrate was determined to be 0.2 OD units/ml, 5.2 ml of the Mv1Lu, and 8.7 ml H292 cell suspensions were, added to 86.1 ml of culture medium, in order to provide an acceptable working ratio of each cell type (i.e., it was a preparation of diluted mixed cells). This ratio was devised in order to achieve a confluent monolayer, in which each cell type covered a substantially equivalent surface area within 1-3 days post-planting of the diluted mixed cells. Prior to dispensing, care was taken to prepare homogenous suspensions of diluted mixed cells. The mixed cells were dispensed at 0.75 ml per glass shell vial (i.e., glass vial containing a sterile glass coverslip). After planting, the vials were allowed to sit for 60 minutes at ambient temperature so that the cells could settle by gravity and produce a more optimum cell distribution of each cell type. The mixed cells were then incubated for 1-3 days at 36° C. in 5% $CO_2$, at 95% relative humidity. Subsequently, the shell vials were stored at ambient temperature to maintain each cell type at substantively equivalent surface ratios for up to 10 days from achieving confluency.

Samples and Processing

Nasopharyngeal specimens submitted to a diagnostic virology laboratory were obtained from patients exhibiting influenza-like symptoms. The specimens were centrifuged to produce a cell pellet for direct antigen testing, and a specimen supernatant for inoculation of various cell cultures. The cell pellet was resuspended in phosphate buffer to prepare a cell suspension and 25 1 portions of the cell suspension were spotted onto a glass slide and dried. Each spot of cells on the slide were then fixed with fixative (e.g., acetone), and incubated for 30 minutes with individual antibody solutions (Bartel's) capable of recognizing various respiratory viruses, including influenza A and RSV, as well as other respiratory viruses. A second antibody solution containing fluorescein (FITC) labelled goat anti-mouse antibodies and counterstain (Bartel's) was added to cover each cell spot on the slides, and incubated for an additional 30 minutes at 35-37° C. The counterstain in the FITC-goat anti-mouse antibody solution contains Evans Blue, which stains the cells and appears red under fluorescence. Slides prepared from the nasopharyngeal specimens were observed for positive (i.e., virus-infected), apple green staining fluorescent cells, using epifluorescence at 100-400× magnification.

In addition, 0.2 ml aliquots of the specimen supernatant were inoculated onto various cell cultures prepared in shell vials containing glass coverslips. The cell cultures included primary rhesus monkey kidney cells (PRMK; ViroMed or BioWhittaker), Mv1Lu cells (Diagnostic Hybrids) HEp-2 cells (Diagnostic Hybrids), MDCK, A549, and H292 cells, as single cell monolayers, as well as mixed cell monolayers of Mv1Lu and H292 cells, produced as described above.

Each inoculated shell vial was centrifuged for 60 minutes at 700×g, and then incubated for 1-3 days at 36° C., in appropriate culture medium (e.g., EMEM containing 0.5 to 2% FBS, 2 mM L-glutamine, and penicillin/streptomycin [100 Units/100 g per ml of medium each]). After incubation, the culture medium was decanted, and the cells were fixed to the glass coverslip with a solution of acetone and methanol (50:50, v/v). An antibody solution (Chemicon or Bartel's) containing a pool of monoclonal antibodies, to multiple respiratory viruses, including Influenza A and RSV, as well as other respiratory viruses was added to cover each coverslip. The coverslips were then incubated for 30 minutes at 35-37° C. The antibody solution was then removed and the coverslips were rinsed with PBS. A second antibody solution containing fluorescein (FITC) labelled goat anti-mouse antibodies and counterstain (Bartel's) was added to cover each coverslip, and incubated for an additional 30 minutes at 35-37° C. The counterstain in the FITC-goat anti-mouse antibody solution contains Evans Blue, which stains the cells and appears red under fluorescence. Shell vial coverslips prepared from the nasopharyngeal specimens (i.e., inoculated cultures) were observed for positive (i.e., virus-infected), apple green staining, fluorescent cells, using epifluorescence at 100-400× magnification.

Results

Some specimens demonstrated a positive direct antigen reaction on the cell spot incubated with Influenza A monoclonal antibody. These specimens also demonstrated fluorescent staining on the single cell Mv1Lu coverslip and the Mv1Lu/H292 mixed cell coverslip, but no or very little fluorescence on the single cell H292 coverslip. The H292 cells are either not susceptible to this strain of Influenza A, or are significantly less susceptible, such that infection is not detectable. Additionally, in some cases (i.e., in specimens with low virus titers), the culture systems were more sensitive than the direct antigen detection method. Also, while the single PRMK cell cultures (i.e., the "gold standard" cells used to detect Influenza A) were positive for the presence of Influenza A, with many specimens, the numbers of infected cells and the total of number of positive specimens were lower, than those identified as positive by the mixed cell monolayers.

In addition, both the MDCK and PRMK cells missed one low titer specimen positive for Influenza A by direct antigen testing (IFA), and one other specimen that was also positive for Influenza A by IFA, while the Mv1Lu cells detected the virus in all of the samples determined to be positive based on direct antigen detection (IFA).

Some specimens demonstrated a positive direct antigen reaction on the cell spot incubated with RSV monoclonal antibody. These specimens also demonstrated fluorescent staining on the single cell H292 coverslip and the MV1Lu/H292 mixed cell coverslip, but no or very little fluorescence on the single cell MV1Lu coverslip. H292 cells are susceptible to RSV infection, while Mv1Lu cells are not susceptible (or are significantly less susceptible, such that infection is not detectable). In addition to the mixed cell cultures, HEp-2 cells (i.e., the "gold standard" cells used to detect RSV) were also observed for the presence of RSV; the performance of HEp-2 cells was generally less sensitive than that of the Mv1Lu and H292 mixed cell monolayers, or the H292 single cell monolayers. The results obtained from testing Influenza A in mink lung cells was very surprising, as the detection of Influenza A using these cells has previously not been described.

Adenoviruses identified from five clinical specimens based on direct antigen testing (IFA) were detected in the H292 and cell culture mixes, while the PRMK cells missed two of the low titer specimens (i.e., there were two false negatives). Thus, H292 and the mixed cultures were more sensitive than PRMK for detection of adenoviruses. While the A549 cells may provide slightly more positive cells, the 292 cells, mixed cell cultures, and A549 cells detected an equal number of positive specimens.

Parainfluenza viruses were also detected in the H292 and mixed cell cultures, while the PRMK cells missed one low titer specimen.

These results clearly show that the mixed cell cultures were equal in sensitivity to the single cell (H292 and Mv1Lu) cultures. Thus, the mixed cells provide savings in material, time, space, and labor, while providing the same level of sensitivity in the detection of respiratory viruses as single cell cultures presently commonly used in diagnostic virology laboratories.

Influenza B Specimens

In addition to the samples discussed above, various dilutions of multiple Influenza B strains obtained from the ATCC were tested in MDCK, Mv1Lu, and PRMK cells. The following Table provides the results of these experiments. In this Table, "MD" refers to the "Maryland" strain, "HK" refers to the "Hong Kong" strain, "TW" refers to the "Taiwan" strain, and "MA" refers to the "Massachusetts" strain:

TABLE 3

Comparison of Influenza B Virus Detection From Prototype Viruses by MDCK, ML, and PRMK Cells

| Influenza B Virus Strain | Virus Dilution | Cell Line | | |
|---|---|---|---|---|
| | | MDCK | Mv1Lu | PRMK |
| MD | $10^{-4}$ | + | + | + |
| | $10^{-5}$ | + | + | + |
| | $10^{-6}$ | − | + | − |
| HK | $10^{-4}$ | + | + | + |
| | $10^{-5}$ | + | + | − |
| | $10^{-6}$ | − | − | − |
| TW | $10^{-4}$ | + | + | + |
| | $10^{-5}$ | + | + | + |
| | $10^{-6}$ | − | − | − |
| MA | $10^{-4}$ | + | + | + |
| | $10^{-5}$ | + | + | + |
| | $10^{-6}$ | + | + | + |

These results indicate that Mv1Lu, MDCK, and PRMK are comparable for the detection of multiple Influenza B virus strains. Thus, these cell lines were identified as good candidates for mixed cell cultures, as well as single cell cultures for the identification of this virus.

Example 3

Detection of CMV in Mixed Cell Cultures

In this Example, mixed cell cultures of Mv1Lu and NCI-H292 cells were used to detect the presence of human cytomegalovirus (HCMV).

The Towne strain of HCMV (ATCC #VR977) was amplified in MRC-5 cells to a titer of greater than $10^6$/ml, and frozen at $-85°$ C. in EMEM containing 10% FBS. Serial dilutions of HCMV were prepared and inoculated into single monolayers of mink lung (Mv1Lu) cells, MRC-5 cells, and mixed cell monolayers of Mv1Lu and H292 cells. Each infected cell culture system was centrifuged for 60 minutes at 700×g, and then incubated for 24 hours at 36° C. in 5% $CO_2$, in appropriate culture medium (e.g., EMEM containing 10% FBS). The culture medium was removed and the cells were fixed to the glass coverslip using a solution of 80% acetone in water. A sufficient amount of HCMV antibody solution (Chemicon) was added to cover each coverslip and incubated for 30 minutes at 35-37° C. The antibody solution was removed, and the coverslip was rinsed with PBS. A second antibody solution consisting of FITC-labelled goat anti-mouse antiserum was added to cover each coverslip and incubated an additional 30 minutes at 35-37° C. The specimens were then observed under epifluorescence at 100-400× magnification for positive (i.e., CMV-infected), nuclear staining, fluorescent cells.

As described in previous Examples, the counterstain in the FITC-labelled goat anti-mouse antibody solution contains Evans Blue, which stains the cells and appears red, when excited by fluorescent light. Fluorescent, apple green nuclear stain was observed in the Mv1Lu single cell monolayer and in the mixed cell monolayers, but not in the H292 cells, as the Mv1Lu cells are susceptible to HCMV infection, while H292 cells are not (or the H292 cells are significantly less sensitive). The MRC-5 cells (i.e., the "gold standard" cells for detection of HCMV) performed about the same as the mixed cell monolayer, as these cultures had a similar number of infected cells as the cells in the mixed monolayer.

Example 4

Detection of Enteroviruses in Mixed Cell Cultures

In this Example, mixed cell cultures were used to detect the enteroviruses, Coxsackie B virus and Echovirus. In these experiments, a mixed cell monolayer of BGMK and NCI-H292 cells were used.

Confluent T-225 flasks of BGMK and H292 cells were prepared in EMEM with 25 mM HUES, 10% FBS, 2 mM L-glutamine, and 50 μg/ml gentamicin. The cells were harvested by first rinsing in 30 ml HBSS without magnesium and calcium, and were then dissociated from the flasks by a brief treatment of 7 ml trypsin-EDTA solution (as described in Example 1). Then, an additional 30 ml of culture medium (EMEM with HEPES, 10% FBS, 2 mM L-glutamine, and 50 μg/ml gentamicin) was added to the suspension to produce a cell suspension concentrate. The optical density at 500 nm was determined for each suspension, using 3 ml of cells. Typically, the OD reading was 0.2/ml for both the BGMK and H292 cell suspensions.

Next, 3 ml of BGMK cell suspension and 8 ml of H292 cell suspension (both suspensions were at 0.2 OD units/ml) were added to 29 ml of the culture medium (25 mM HEPES, 10% FBS, 2 mM L-glutamine, and 50 μg/ml gentamicin) to provide an acceptable working ratio of each cell type in a diluted mixed cell suspension. This ratio was intended to achieve a confluent monolayer consisting of each cell type covering substantially equivalent surface area within 1-3 days post-planting of the diluted mixed cells. Care was exercised to prepare a homogenous suspension of diluted mixed cells prior to dispensing 0.75 ml to each of 100 glass shell vials, each of which contained a sterile glass coverslip. The vials were allowed to sit for 60 minutes post-planting at ambient temperature to allow the cells to settle by gravity and produce a more optimum cell distribution. The vials were then were moved to an incubator for incubation at 36° C. for 1-3 days in 5% $CO_2$, at 95% relative humidity.

Stock virus suspensions and clinical specimens shown to contain Coxsackie B virus or echovirus were used to infect BGMK/H292 cell mixtures, as well as single cell monolayers of BGMK, H292, MRC-5, and PRMK cells. For clinical samples, throat swab, nasopharyngeal swab, sputum, stool, and rectal swabs were collected from patients, placed in viral transport medium, and filtered through 0.45 m filter to remove possible bacterial and fungal contaminants prior to inoculation of cell cultures. Cerebrospinal fluid (CSF) collected from patients was placed in viral transport medium, and used directly for inoculation of cells. For inoculation of shell vials, the media present in the vials were removed and fresh media added. Then, 0.2 ml of specimen was inoculated into each vial. The inoculated vials were centrifuged at 700×g for 45-60 minutes at room temperature. Subsequently, the vials were incubated at 37° C. for 1-3 days, and viral presence was detected using immunofluorescent staining.

For staining, the medium was removed from each vial and the cells were fixed on the coverslip with acetone. The coverslip was removed from each vial, and stained with 25 l primary antibody (mouse monoclonal antibody directed against enteroviruses [Dako]), for 30 minutes at 37° C. After washing with PBS, 25l of the FITC-conjugated anti-mouse Ig (Dako) was used as a secondary antibody for staining, and incubated at 37° C. for 30 minutes. After another wash, the coverslips were mounted on slides and observed under fluorescence. The presence of one or more specific fluorescent-stained cells on the coverslip was considered positive. As described in previous Examples, the counterstain in the FITC-labelled goat anti-mouse antibody solution contains Evans Blue, which stains the cells, and appears red upon exposure to fluorescent light. For Coxsackie B virus detection, fluorescent, apple green stain was observed in many of the BGMK cells in the BGMK single cell monolayer and in the mixed cell monolayers primarily in the BGMK cells, but not in as many H292 cells, as BGMK cells are more susceptible to Coxsackie B virus infection. For some types of Coxsackie B virus isolates, H292 Cells are not as susceptible (or the H292 cells are significantly less susceptible). The "gold standard" cell line (i.e., PRMK cells) did not exhibit the same number of infected cells as the mixed cell monolayers.

For detection of echovirus, fluorescent, apple green stain was observed in many H292 cells in the H292 single cell monolayer and in the mixed cell monolayers, primarily in the H292 cells, but not in as many BGMK cells. H292 cells are more susceptible to echovirus infection, while BGMK cells are not as susceptible (or the BGMK cells are significantly less sensitive). The "gold standard" line (i.e., MRC-5 cells) performed, but did not appear to have as many infected cells as the mixed cell monolayers. In the case of the BGMK/H292 mixed cell monolayers infected with high titer samples of enteroviruses, cell-specific virus mediated cytopathic effect (CPE) was evident (i.e., the CPE was observed in BGMK cells when Coxsackie B virus was present at high titer, and CPE was observed in H292 cells when echovirus was present at high titer).

Example 5

Detection of Herpes Simplex Virus and HCMV in Mixed Cell Cultures

In this Example; mixed cell cultures are used to detect herpes simplex virus (HSV) and HCMV, using a mixed cell monolayer of genetically engineered baby hamster kidney (BHK) cells (e.g., ATCC #CCL-12072) and Mv1Lu cells.

The BHK and Mv1Lu cells are grown in flasks, trypsinized, and mixed as described in previous Examples, such that a suitable dilution of mixed cells is produced. These mixed cell dilutions are then used to inoculate sterile glass shell vials containing coverslips, as described above. The cells are then centrifuged and inoculated with virus or clinical samples, incubated, and fixed, as described above.

HCMV is detected in the Mv1Lu cells, using antibody as described in Example 3 above, while HSV (HSV-1 and HSV-2) is identified using a β-galactosidase staining kit (i.e., detecting the reporter gene induced by the virus infecting the genetically engineered BHK cells).

Example 6

Detection of Respiratory Viruses in Mixed Cell Cultures

In this Example, mixed cell cultures are used to detect a panel of respiratory viruses. In these experiments, three cell types are combined to produce a mixed cell culture that is capable of detecting at least three viruses.

First, A549, H292, and mink lung (e.g., Mv1Lu) cells are grown in flasks, trypsinized, and mixed as described in previous Examples, such that a suitable dilution of mixed cells is produced. In preferred embodiments, the cells are diluted such that the mixed cells in, culture will be in approximately the same proportions (i.e., 1:1:1). These mixed cell dilutions are then used to inoculate sterile glass shell vials containing coverslips, as described above. The cells are then centrifuged and inoculated with virus or clinical samples, incubated, and fixed, as described above.

The viruses capable of infecting these cells are detected and identified using the methods described in Example 2, above. In these mixed cell cultures, the 292 cells are used to detect the presence of parainfluenza viruses and RSV, while the A549 cells are used to detect the presence of adenoviruses, and the mink lung cells are used to detect the presence of influenza viruses (e.g., Influenza A and B).

Example 7

Detection of HSV and *Chlamydia* in Mixed Cell Cultures

In this Example, mixed cell cultures are provided which allow the detection of two organisms commonly associated with sexually transmitted diseases. In these experiments, mink lung cells (e.g., Mv1Lu) useful for the detection of HSV are mixed with McCoy cells useful for the detection of *C. trachomatis*.

First, McCoy cells and mink lung (e.g., Mv1Lu) cells cells are grown in flasks, trypsinized, and mixed as described in previous Examples, such that a suitable dilution of mixed cells is produced. In preferred embodiments, the cells are diluted such that the mixed cells in culture will be in approximately the same proportions. These mixed cell dilutions are then used to inoculate sterile glass shell vials containing coverslips, as described above. The cells are then centrifuged and inoculated with samples (e.g., clinical samples), incubated, and fixed, as described above.

The organisms capable of infecting these cells (e.g., HSV infects the mink lung cells, while *C. trachomatis* infects the McCoy cells) are detected and identified using the methods described in Example 2, above. As with the other mixed cell culture systems, the presence of virus and/or *C. trachomatis* may be detected by other methods, such as the observation of CPE, animal inoculation, etc. Thus, it is not intended that the mixed cell culture assay systems of this Example or any of the preceding examples be limited to any particular method of microorganism detection, identification, and/or quantitation.

Example 8

Evaluation of Single Cell Cultures and Mixed Cell Cultures for Detection of Respiratory Viruses This Example evaluated different cell lines individually and in mixed cell culture. The following cell lines were used in the exemplary shell vial with coverslip format: R-mix (i.e., Mv1Lu and A549): C961023; Mv1Lu: C581023; A549: C561023; canine kidney MDCK: C831022; NCI-H292: C591023; LLC-MK2; C861022; CV1; C521023; pRHMK: -CA-491016; MDCK/A549: C501022; MDCK/H292: C102303; Mv1Lu-hF Clones numbers 15B, 17, 18, 29, 30, 35, 38 all 10-23-03.

The following reagents and virus strains were used: RM03T; Influenza A: WS, Port Chalmers, Victoria, and Mai; Influenza B; Taiwan and G1; RSV: 031203 and 042403; Adenovirus: #1 and #5; Parainfluenza 1; Parainfluenza 2; Parainfluenza 3; $D^3$ Kit; 091603; and Solution 1: 011303D.

Briefly, shell vials were all re-fed with 1 ml of RM03T. Virus dilutions were all in RM03T. Shell vials were inoculated in duplicate with dilutions of each of the 7 respiratory viruses, i.e., influenza A, influenza B, RSV, adenovirus, parainfluenza 1, parainfluenza 2, and parainfluenza 3. Shell vials were centrifuged for 1 hour at 700×g then placed in a 35-37° C. incubator. 24 hours, 48 hours and 72 hours post inoculation, a set of shell vials were fixed and stained with Solution 1 and $D^3$.

The following is a key to the results shown in the following Tables 4-9: s=small. B=Bursts. ~=Approximately. TNTC=Too numerous to count. 1+=25% of Monolayer infected. 2+=50% of Monolayer infected. 3+=75% of Monolayer infected, 4+=100% of Monolayer infected. N/A=Not Available. F=Field (there are 44 fields per monolayer.)

TABLE 4

24 Hour Post Inoculation Results Using Influenza A Virus, Influenza B Virus, RSV, and Adenovirus

| | Influenza A: | | | |
|---|---|---|---|---|
| | WS | Victoria | Port Chalmers | Mai |
| R-mix | 99, 95 | 113, 127 | 197, 243 | 88, N/A |
| Mv1Lu | 105, 114 | 142, 150 | ~5/F | 169, 161 |
| A549 | N/A | N/A | N/A | N/A |
| MDCK | 70 + ~8sB, 80 + 10sB | 3sB + 71, 2sB + 69 | 2sB + 68, 2B + 88 | 2sB + 90, 3sB + 100 |
| H292 | 12, 5 | 17, N/A | 12, 38 | N/A, 7 |
| LLC-MK2 | 11, 7 | 18, 19 | 38, 28 | 5, 2 |
| CV1 | 8, 7 | 23, 40 | 15, 12 | N/A, 3 |
| pRHMK | ~15B + ~10 | 5B + 50, 5B + 62 | 1+ | 5bigB, 1bigB + 5 |

TABLE 4-continued

24 Hour Post Inoculation Results Using Influenza
A Virus, Influenza B Virus, RSV, and Adenovirus

| | | | | |
|---|---|---|---|---|
| MDCK/A549 | TNTC + Bursts | 2B + 4sB + 75, 1sB + 104 | 145, 1B + 162 | 3bigB + 77, N/A |
| MDCK/H292 | TNTC + Bursts | 67, 73 | 1sB + 84, 3B + 101 | 1bigB + 3sB + 69, 1B + 3sB + 101 |
| 15B | 121, 124 | 3sB + 167, 6sB + 169 | ~300 | ~300 |
| 17 | 168 + 2B, 150 | 132, 133 | ~200 | 5/F |
| 18 | 113, 120 | 3sB + 166, 171 | 241, 260 | 222, 200 |
| 29 | 135, 152 | 109, 114 | ~200 + ~4sB | 5/F |
| 30 | 109 + 1B, 125 | 133, 141 | ~300 | 6/F |
| 35 | 75, 97 | 137, 140 | ~200 | 129, 170 |
| 38 | 136, 132 | 113, 126 | ~300 | 5/F |

Influenza B:

| | Taiwan | G1 |
|---|---|---|
| R-mix | 4/F | 9/F |
| Mv1Lu | 9/F | 12/F |
| A549 | N/A | N/A |
| MDCK | 14B + 4/F, 8B + 4/F | 9B + 6/F, 16B + 6/F |
| H292 | 5, 8 | 13, N/A |
| LLC-MK2 | 54, 50 | 16, 10 |
| CV1 | 72, 80 | 45, N/A |
| pRHMK | 3B + 114, 2B + 128 | 39, 49 |
| MDCK/A549 | 2+ | 2+ |
| MDCK/H292 | 1+ | 1+ |
| 15B | 11/F | 10/F |
| 17 | 10/F | 15/F |
| 18 | 12/F | 12/F |
| 29 | 9/F | 9/F |
| 30 | 10/F | 9/F |
| 35 | 7/F | 8/F |
| 38 | 9/F | 10/F |

RSV:

| | 031203 | 042403 |
|---|---|---|
| R-mix | 54, 47 | 13, 16 |
| Mv1Lu | 33, 27 | 3, 7 |
| A549 | 34, 24 | 18, 23 |
| MDCK | 0, 0 | 0, 0 |
| H292 | 23, 26 | 25, 22 |
| LLC-MK2 | 30, 33 | 3, 6 |
| CV1 | 20, 23 | 8, 9 |
| pRHMK | 0, 0 | 0, 0 |
| MDCK/A549 | 23, 25 | 10, 13 |
| MDCK/H292 | 28, 18 | 15, 19 |
| 15B | 34, 38 | N/A |
| 17 | 43, 37 | N/A |
| 18 | 26, 30 | N/A |
| 29 | 18, 30 | N/A |
| 30 | 18, 24 | N/A |
| 35 | 21, 22 | N/A |
| 38 | 28, 40 | N/A |

Adenovirus:

| | Adenovirus #1 | Adenovirus #5 |
|---|---|---|
| R-mix | 20/F | ~300 |
| A549 | 20/F | 216, 220 |
| H292 | 5/F | 46, 57 |
| LLC-MK2 | 0, 0 | 0, 0 |
| CV1 | 0, 5 | 0, 0 |
| pRHMK | 15/F | 116, 160 |
| MDCK | 0, 0 | 0, 0 |
| MDCK/A549 | 5/F | 139, 124 |
| MDCK/H292 | 55, N/A | 4, 6 |

TABLE 5

24, 48 and 72 Hour Post Inoculation Results Using Parainfluenza 1

| | 24 hour | 48 hour | 72 hour |
|---|---|---|---|
| R-mix | 64, N/A | 143, 160 | 134, 143 |
| Mv1Lu | 69, 73 | 118, 109 | 80, 88 |
| A549 | 90, 194 | 111, 100 | 121, 110 |
| MDCK | 0, 0 | 0, 2 | 0, 0 |
| H292 | 98, 111 | 158, 162 | 170, 159 |
| LLC-MK2 | 88, 106 | 163, 158 | 121, 117 |
| CV1 | 75, 66 | 68, 73 | 60, 72 |
| pRHMK | 25sB + 25, 6sB + 40 | 4+ | 4+ |
| MDCK/A549 | 41, 50 | 62, 80 | 120, 122 |
| MDCK/H292 | 38, 40 | 68, 75 | 68, 80 |
| 15B | 49, 54 | 110, 90 | ~100 |
| 17 | 58, 63 | 119, 50B + 100 | ~120 |
| 18 | 66, 62 | 87, 95 | ~100 |
| 29 | 69, 65 | 63, 66 | ~70 |
| 30 | 23, 30 | 102, 115 | ~100 |
| 35 | 47, 58 | 72, 75 | ~75 |
| 38 | 50, 44 | 80, 85 | ~80 |

TABLE 6

24, 48 and 72 Hour Post Inoculation Results Using Parainfluenza 2

| | 24 hour | 48 hour | 72 hour |
|---|---|---|---|
| R-mix | 66, N/A | 1+ | 3+ |
| Mv1Lu | 6, 10 | ~25 | ~20sB |
| A459 | 210, 217 | 2+ | 4+ |
| MDCK | 0, 0 | 0, 0 | 0, 0 |
| H292 | 116, 106 | 2+ | 4+ |
| CV1 | 84, 94 | 1+ | 4+ |
| pRHMK | 73, 80 | 2+ | 4+ |
| LLC-MK2 | 33, 29 | ~15B + 30, N/A | 1+ |
| MDCK/A549 | 21, 28 | ~75 | 1+ |
| MDCK/H292 | 15, 24 | ~50 | 1+ |

TABLE 7

24, 48 and 72 Hour Post Inoculation Results Using Parainfluenza 3

| | 24 hour | 48 hour | 72 hour |
|---|---|---|---|
| R-mix | 5/F | TNTC | 4+ |
| Mv1Lu | 3/F | ~50BB | ~50BB |
| A459 | 1+ | 4+ | 4+ |
| MDCK | 0, 0 | ~25 | 3/F |
| H292 | 4/F | TNTC | 4+ |
| CV1 | 1+ | 4+ | 4+ |
| pRHMK | 1+ | 4+ | 4+ |
| LLC-MK2 | 4/F | TNTC | 4+ |
| MDCK/A549 | ~50 | 1+ | 4+ |
| MDCK/H292 | ~50 | 1+ | 4+ |

TABLE 8

48 Hour Post Inoculation Results Using Influenza
A, Influenza B, RSV, and Adenovirus Influenza A:

| | WS | Victoria | Port Chalmers | Mai |
|---|---|---|---|---|
| R-mix | 79, 70 | 66, 72 | 128, 120 | 92, 67 |
| Mv1Lu | 60, 49 | 131, 127 | 94, 82 | 97, 94 |
| A549 | N/A | N/A | N/A | N/A |
| MDCK | 4+ | 2+ | 2sB + 50, 47 | 1+ |
| H292 | 8, 11 | 9, 13 | 2, 2 | 7, 10 |
| LLC-MK2 | 19, 25 | 1sB + 27, 31 | 55, 47 | 15, 10 |
| CV1 | 8, 21 | 24, 28 | 60, 48 | 6, 9 |

TABLE 8-continued

48 Hour Post Inoculation Results Using Influenza A, Influenza B, RSV, and Adenovirus

| pRHMK | 3+ | 4+ | 4+ | 4+ |
|---|---|---|---|---|
| MDCK/A549 | 4+ | 4+, 2+ | 1+ | 2+, 3+ |
| MDCK/H292 | 4+ | 1bigB, 2+ | 1B + 30, 2+ | 13B + ~100, 4+ |
| 15B | 77, 81 | 6sB + 75, 1+ | 140, 160 | 100, 119 |
| 17 | 67, 65 | 76, 80 | 104, 113 | 124, 130 |
| 18 | 51, 61 | 66, 3sB + 100 | 133, 118 | 110, 105 |
| 29 | 76, 60 | 2sB + 85, 91 | 143, 160 | 139, 115 |
| 30 | 86, 70 | 56, 6B | 150, 140 | 177, 160 |
| 35 | 32, 40 | 43, 1sB + 52 | 87, 80 | 90, 83 |
| 38 | 74, 1+ | 4sB + 81, 2sB + 88 | 4sB + 100, 6sB + ~100 | 118, 108 |

Influenza B:

| | Taiwan | G1 |
|---|---|---|
| R-mix | 61, 64 | 120, 115 |
| Mv1Lu | 45, 65 | 120, 110 |
| A549 | N/A | N/A |
| MDCK | 4+ | 4+ |
| H292 | 1, 0 | 2, 2 |
| LLC-MK2 | 34, 33 | 11, 16 |
| CV1 | 23, 24 | 17, 19 |
| pRHMK | ~10big B | 35, 2big B |
| MDCK/A549 | 4+ | 4+ |
| MDCK/H292. | 3+ | 4+ |
| 15B | 100, N/A | 147, 152 |
| 17 | 80, 83 | 153, 149 |
| 18 | 102, N/A | 136, 141 |
| 29 | 71, 73 | 74, 70 |
| 30 | 83, 96 | 100, 94 |
| 35 | 60, 53 | 108, 95 |
| 38 | 70, 65 | 77, 72 |

RSV:

| | 031203 | 042403 |
|---|---|---|
| R-mix | 60, 70 | 32, 39 |
| Mv1Lu | 53, 50 | 2, 9 |
| A549 | 44, 43 | 23, 28 |
| MDCK | 0, 0 | 0, 0 |
| H292 | 40, 37 | 33, 54 |
| LLC-MK2 | 28, 35 | 13, 13 |
| CV1 | 26, 18 | 8, 7 |
| pRHMK | 0, 0 | 0, 0 |
| MDCK/A549 | 22, 6 | 12, 15 |
| MDCK/H292 | 19, 24 | 18, 18 |
| 15B | 39, 42 | N/A |
| 17 | 68, 70 | N/A |
| 18 | 54, 57 | N/A |
| 29 | 38, 50 | N/A |
| 30 | 32, 31 | N/A |
| 35 | 50, 32 | N/A |
| 38 | 50, 66 | N/A |

Adenovirus:

| | Adenovirus #1 | Adenovirus #5 |
|---|---|---|
| R-mix | 3+ | 3+ |
| A549 | 3+ | 3+ |
| H292 | 3+ | 2+ |
| LLC-MK2 | 8/F | 4/F |
| CV1 | 70, 62 | 35, 40 |
| pRHMK | 2+ | 1+ |
| MDCK | 2, 0 | 1, 0 |
| MDCK/A549 | 1+ | 1+ |
| MDCK/H292 | 1+ | 1+ |

TABLE 9

72 Hour Post Inoculation Results Using Influenza A, Influenza B, RSV, and Adenovirus Influenza A:

| | WS | Victoria | Port Chalmers | Mai |
|---|---|---|---|---|
| R-mix | <25 | ~25 | ~50 | 1sB + ~30 |
| Mv1Lu | <10 | ~25 | ~25 | ~25 |
| A549 | N/A | N/A | N/A | N/A |
| MDCK | 4+ | 2+, 4+ | 1+, ~50 | 3+, 2+ |
| H292 | <5 | <10 | <5 | <10 |
| LLC-MK2 | <5 | <25 | <5 | <10 |
| CV1 | <5 | <25 | ~10 | <10 |
| pRHMK | 4+ | 4+ | 4+ | 4+ |
| MDCK/A549 | 4+ | 1+, 4+ | 4+ | 4+ |
| MDCK/H292 | 4+ | ~20B, 4+ | 1+, 4+ | 4+ |
| 15B | ~25 | 12sB, ~25 | ~25 | ~25 |
| 17 | ~25 | <5 | ~25 | ~25 |
| 18 | <10 | 3B + 50, ~25 | ~25 | ~50 |
| 29 | ~10 | ~15sB, ~25 | ~25 | ~25 |
| 30 | <10 | <10 | ~25 | ~50 |
| 35 | <10 | <25 | <5 | ~25 |
| 38 | ~2sB + ~50 | 50, 25 | ~25 | ~50 |

Influenza B:

| | Taiwan | G1 |
|---|---|---|
| R-mix | 8, 17 | ~30 |
| Mv1Lu | 0, 0 | <5 |
| A549 | N/A | N/A |
| MDCK | 4+ | 4+ |
| H292 | <5 | <5 |
| LLC-MK2 | 7, 10 | 5, 7 |
| CV1 | <5 | <5 |
| pRHMK | 4+ | <5, 4+ |
| MDCK/A549 | 4+ | 4+ |
| MDCK/H292 | 4+ | 4+ |
| 15B | 0, 0 | <5 |
| 17 | <5 | <5 |
| 18 | 0, 0 | <5 |
| 29 | 0, <5 | <5 |
| 30 | 0, <5 | <5 |
| 35 | <5 | <5 |
| 38 | <5 | <5 |

RSV:

| | 031203 | 042403 |
|---|---|---|
| R-mix | 59, 50 | 24, 27 |
| Mv1Lu | 45, 52 | 7, 20 |
| A549 | 60, 56 | 24, 36 |
| MDCK | 0, 0 | 0, 0 |
| H292 | 26, 30 | 50, N/A |
| LLC-MK2 | 31, 28 | 8, N/A |
| CV1 | 25, 31 | 13, 19 |
| pRHMK | 2, 1 | 3, 5 |
| MDCK/A549 | 13, 16 | 17, 19 |
| MDCK/H292 | 21, 30 | 12, 16 |
| 15B | 39, 45 | N/A |
| 17 | 38, 42 | N/A |
| 18 | 40, 47 | N/A |
| 29 | 30, 35 | N/A |
| 30 | 34, 30 | N/A |
| 35 | 39, 35 | N/A |
| 38 | 40, 43 | N/A |

Adenovirus:

| | Adenovirus #1 | Adenovirus #5 |
|---|---|---|
| R-mix | 3+ | 4+ |
| A549 | 4+ | 4+ |
| H292 | 2+ | 2+ |
| LLC-MK2 | 1+ | 1+ |
| CV1 | 4/F | 4/F |
| pRHMK | 2+ | 2+ |

TABLE 9-continued

| 72 Hour Post Inoculation Results Using Influenza A, Influenza B, RSV, and Adenovirus | | |
|---|---|---|
| MDCK | 0, 0 | 0, 0 |
| MDCK/A549 | 2+ | 2+ |
| MDCK/H292 | 1+ | 1+ |

The above data show that the mixed cell cultures of MDCK+A549 and MDCK+H292 showed comparable sensitivity to R-mix, i.e., Mv1Lu and A549 cells with respect to detecting the seven exemplary respiratory viruses: respiratory syncytial virus (RSV), adenovirus, parainfluenza 1 virus, parainfluenza 2 virus and parainfluenza 3 virus. In one embodiment, mixtures of MDCK with one or more of A549 and H292 cells may preferably be used at 24 hours in culture since, by 48 and 72 hours, the MDCK almost completely outgrew the other cell lines.

Example 9

Comparison of MDCK and Mv1Lu Cells Inoculated with Influenza A and B

This example was carried out to determine the ability of MDCK and Mv1Lu cells to propagate strains of Influenza A and B. Cultures were tested using duplicate monolayers at 24; 48 and 72 hours post inoculation. Where virus is replicating, more positive cells (such as those detected by fluorescence) were expected by the inventors to be observed at the 48 and 72 hour time points compared to the zero time point of inoculation.

The following exemplary cells and viruses were used: MDCK lot C830807; Mv1Lu lot C580807R; RM03T lot 070903E; ELVIS Solution 1 lot 061203 (Diagnostic Hybrids, Inc., Ohio, USA); Influenza A and Influenza B components from $D^3$ Kit lot 011303; ELVIS Mounting Fluid lot 011603A (Diagnostic Hybrids, Inc., Ohio, USA).

Briefly, cell cultures of MDCK and Mv1Lu shell vials with coverslips were used. All cultures were re-fed with 1 ml of RM03T. Virus stocks were rapidly thawed in a 35-37° C. bath and diluted to a working stock in RM03T. Each culture was inoculated in duplicate with 2001 of each working virus stock. All cultures were centrifuged at 700×g for 1 hour. All cultures were placed in a 35-37° C. incubator. A set of each was processed according to the $D^3$ Kit product insert at 24, 48 and 72 hours post inoculation.

TABLE 10

| Comparison of MDCK and Mv1Lu cells Using Influenza A and Influenza B | | | | | | |
|---|---|---|---|---|---|---|
| | MDCK | | | Mv1Lu | | |
| Virus/strain/lot # | Day 1 | Day 2 | Day 3 | Day 1 | Day 2 | Day 3 |
| Flu A: Denver: 112701N | 156, 129 + 1B | ~15/F + 5BB | 4+ CPE | *179, 164* | *110, 115* | *~25* |
| Flu A: Aichi: 112701K | 189, 206 + 1B | 100, 80 | ~100 + 1B | *~7/F* | *~6/F* | *~60* |
| Flu A: PR: 111201D | 114 + 5B, 118 + 4B | ~1+ CPE | ~50 | *147, 158* | *50, 42* | *~4* |
| Flu A: Victoria: 121800 | 121 + 2B, 106 | 1+ CPE | ~30 + ~5B | *171, 208* | *1+ CPE* | *1+ CPE* |
| Flu A: WS: 111201E | 118 + 1BB, 120 + 7B | 3+ CPE | 4+ CPE | *87, 122* | *1+ CPE* | *3+ CPE* |
| Flu A: Portchalmers: 112701 | 59, 68 | ~5 + 1B | ~100 + ~3B | *105, 98* | *~60* | *~100 + ~2B* |
| Flu A: MaI: 112701L | 106 + 1B, 118 + 3B | ~50 + ~6B | 4+ CPE | *176, 175* | *~100* | *~100* |
| Flu A: HongKong: 112701M | 112 + 1B, 85 + 1B | ~50 + 2B | ~100 | *160, 170* | *~100 + ~10B* | *~100* |
| Flu A: NJ: 102699 | 134 + 2B, 113 + 3B | 2+ CPE | 4+ CPE | *225, 190* | *~85* | *~75* |
| Flu B: GL: 112701S | ~5/F + 1B | 3+ CPE | 4+ CPE | *~10/F* | *~50* | *~50* |
| Flu B: Taiwan: 112701R | ~5/F + ~1B/F | 3+ CPE | 4+ CPE | *~8/F* | *~50* | *~10* |
| Flu B: HongKong: 020402B | *81, 82* | ~10 | ~100 | *125, 140* | *~10* | *~40* |
| Flu B: Mass.: 112701Q | *52, 60* | ~20 | ~20 | *199, 216* | *~30* | *~20* |
| Flu B: Maryland: 112701P | ~75B + tntc S | 3+ CPE | 4+ CPE | *~20/F* | *~50* | *~100 + 1B* |
| Flu B: Russia: 112701FF | ~8/F + ~20B | 2+ CPE | 4+ CPE | *~10/F* | *~40* | *~20* |

123 = number of single fluorescent cells.
B = Burst of fluorescent cells. Usually 100 or more together.
BB = Big Burst. Usually described by percentage of monolayer covered.
S = Single cells.
~ = approximately. Usually used as an average of both monolayers.
+ = and. Unless used before CPE. (See CPE below).
5/F = 5 single cells per field. There are 44 fields per coverslip.
tntc = Too numerous to count.
CPE = cytopathic effect. This ranges from 1+ to 4+ with 1 = 25%, 2 = 50%, 3 = 75% and 4 = 100% of cells infected.
Bold = increasing titer. (virus replication)
*Italic* = decreasing titer. (no virus replication)

In the above experiments, 11/15 virus strains were propagated in the MDCK cell line. Influenza A: Aichi and Flu B: Mass, had lower, titers on days 2 and 3. Influenza A Hong Kong and Influenza A Port Chalmers did not have any significant change in virus titer from 1 to 3 days of culture. The data shows that 2/15 virus strains were propagated in the Mv1Lu cell line. They were Influenza A: Victoria and Influenza A: WS. 11/15 virus stocks cultured in the Mv1Lu lost titer after 24 hours. 2 virus strains remained the same titer over the 3 days in the Mv1Lu cell line. The day 1 results showed the Mv1Lu cells to be slightly more sensitive than MDCKs as measured by the number of positive individual cells, however, the MDCKs were the only cell line to show bursting at 24 hours. Based on this data, there is no significant difference on day 1 initial titer between the Mv1Lu and MDCK cell lines. Surprisingly, MDCK cells detect and produce influenza A and B at higher levels than the Mv1Lu cells.

Thus, the use of MDCK in single cell culture and in mixed cell culture with one or more of H292 and A549 is useful for identifying low levels of influenza A virus and influenza B virus at the exemplary times of 48 and 72 hours post-inoculation, as well as for producing influenza A virus and influenza B virus.

Example 10

Materials and Methods

The following is a brief description of the exemplary materials and methods used in the subsequent Examples.
A. Virus A seed stock of SARS-CoV Urbani that was passaged twice in Vero E6 cells provided by the Centers for Disease Control and Prevention, Atlanta, Ga. This virus was amplified by two passages in Vero E6 cells to establish a high titer stock (passage 4) that was utilized for all experiments. SARS-CoV was titered in Vero E6 cells by $TCID_{50}$, Briefly, cells were plated in 96-well plates (Falcon, Becton Dickson) at a density of $4 \times 10^5$ cells/well in 150 µl of medium, Virus was serially diluted by half logs from $10^0$-$10^{-7}$ in culture medium containing 2% antibiotic-antimycotic (Invitrogen Corporation, Carlsbad, Calif.), 100 µl of each dilution was added per well and cells were incubated 3-4 days at 37° C.
B. Cell Line The following Table lists exemplary cell lines that were used and/or equivalent cells that may be used in the invention's methods, and that are publically available (e.g., from the American Type Culture Collection (ATCC), Rockville, Md., and Diagnostic Hybrids, Inc. (DHI), Athens, Ohio; Cell Bank, Ministry of Health and Welfare, Japan):

TABLE 11

Exemplary Cells Useful In The Invention

| Cells | Sources |
| --- | --- |
| Vero E6 | ATCC # CRL-1586, DHI # 67-0102 |
| MRC-5 | ATCC # CCL-171, DHI # 51-0102 |
| BHK-21 | ATCC # CCL-10, DHI # 89-0102 |
| MDCK | ATCC # CCL-34, DHI # 83-0102 |
| HRT-18 (HCT-18) | ATCC # CCL-244 |
| Mv1Lu | ATCC # CCL-64, DHI # 58-0102 |
| CMT-93 | ATCC # CCL-223 |
| AK-D | ATCC # CCL-150 |
| A549 | ATCC # CCL-185, DHI # 56-0102 |
| HEL | DHI # 88-0102 |
| pRHMK | DHI # 49-T025, DHI # 49-0102 |
| pCMK | DHI # 47-T025, DHI # 47-0102 |
| L2 | ATCC # CCL-149 |
| R-Mix | DHI # 96-T025 |
| HEK-293T | ATCC # CRL-1573; CRL- 11264, CRL-11270; Pear, et al., PNAS USA, Vol 90, pp 8392-8396 September 1993; DuBridge et. al., Mol. Cell. Biol. Vol 7, pp 379-387, 1987; University Dr. Yoshi Kawaoka, Univ. Wisconsin, Madison. |
| Huh-7 (JTC-39) | CellBank #JCRB0403 |

R-Mix (R-Mix FRESHCELLS, Diagnostic Hybrids, Inc., Ohio) is a mixed monolayer of mink lung cells (strain Mv1Lu) and human Adenocarcinoma cells (strain A549). the hAPN expression construct used to create BHK21/hAPN and CMT-93/hAPN was previously described (Wentworth, et al., 2001). Further description of Huh-7 cells is in Nakabayashi et al., Cancer Res., 42: 3858-3863, 1982; Nakabayashi et al., Gann, 75: 151-158, 1984; and Nakabayashi et al., Cancer Res., 45:6379-6383, 1985.

Vero E6, 293T, L2, AK-D, A549, pCMK, pRhMK, Mv1Lu, CMT-93, and R-mix were maintained in Dulbecco's modified Eagle Medium (DMEM) (Invitrogen Corp.) supplemented with 10% fetal bovine serum (FBS) (Hyclone, Logan, Utah) and 2% antibiotic-antimycotic MDCK cells were maintained in DMEM high glucose (Invitrogen Corp.) supplemented with 5% FBS and 2% antibiotic-antimycotic. HEL cells were maintained in Modified Eagle's Medium (MEM) supplemented with 10% FBS and 2% antibiotic-antimycotic. HRT-18 cells were maintained in RPMI 1640 (Invitrogen Corp.) supplemented with 10% horse serum (Hyclone), 1 mM MEM sodium pyruvate (Invitrogen Corp.) and 2% antibiotic-antimycotic. Huh-7 cells were maintained in DMEM supplemented with 20% FBS and 2% antibiotic-antimycotic. MRC-5 cells were maintained in MEM supplemented with 10% FBS, 1 mM sodium pyruvate, 0.1 mM MEM nonessential amino acids (Invitrogen Corp.) and 2% antibiotic-antimycotic. BHK-21 cells were maintained in DMEM supplemented with 10% FBS and 5% tris phosphate buffer (Invitrogen Corp.).
C. PCR Assay G3PDH, genomic. SARS-CoV RNA (gRNA) and subgenomic RNA (sgRNA) were detected using multiplex one-step RT-PCR. Oligonucleotide primers used to amplify the different targets were as follows: G3P-279 (sense) 5' CAT-CACCATCTTCCAGGAGC-3' (SEQ ID NO:7) binds at nt 279-299; G3P-1069R (antisense) 5'-CTTACTCCTTGGAG-GCCATG-3' (SEQ ID NO:8) binds at nt 1069-1049; SARS-21,263 (sense) 5'-TGCTAACTACATTTTCTGGAGG-3' (SEQ ID NO:9) binds at nt 21,263-21,284 of SARS-Urbani; SARS-21,593R (antisense) 5'-AGTATGTTGAGTGTAATT-AGGAG-3' (SEQ ID NO:10) binds at nt 21,593-21,571 of SARS-Urbani; and SARS-1 (sense) 5'-ATATTAGGTTTT-TACCTACCCAGG-3' (SEQ ID NO:11) binds at nt 1-24 of SARS-Urbani, Amplification was carried out using the Qiagen OneStep RT-PCR kit (Qiagen) according to the manufacturer's protocol. Briefly, each reaction consisted of 2 µg of total RNA isolated using TRIZOL Reagent (Invitrogen), 400 µM dNTPs, 200 nM of each G3PDH primer, 400 nM SARS-1, 400 nM SARS-21,263, 600 nM SARS-21,593R and 2 µl Qiagen enzyme mix. The cycling parameters were: 50° C. for 30 min, 95° C. for 15 min, 35 cycles of 94° C. for 30 s, 57-58° C. for 30 s, 72° C. for 1 min, followed by 10 min at 72° C. in an Eppendorf Mastercycler gradient (eppendorf). Amplification products were analyzed by electrophoresis through a 1.5% agarose gel and visualized by ethidium bromide staining. All primers were synthesized by the Molecular Genetics Core (David Axelrod Institute, Wadsworth Center, Albany, N.Y.).

D. Cell Infection

Cells seeded at a density of $2 \times 10^6$ in T25 flasks (Falcon, Becton Dickson) were inoculated with virus at an MOI of 0.001 in a final volume of 1, ml and were incubated 1 h at 37° C. Virus was removed and 5 ml fresh medium added to each flask. Cells were maintained at 37° C. throughout the experiment. At 1, 24 and 48 h post-inoculation (p.i.), cells were observed for CPE, supernatants were collected for subsequent titration and total RNA was extracted using TRIZOL Reagent (Invitrogen Corp.). RNA was quantitated by spectrophotometer (Eppendorf).

Example 11

Exemplary Multiplex RT-PCR Assay for the Detection of SARS-CoV Replication

A RT-PCR assay for the detection of SARS-CoV replication was developed. Replication of corona- and arterivirus RNA occurs through discontinuous synthesis, thought to occur during negative strand synthesis, generating 3' co-terminal nested subgenomic RNAs (sgRNA). The inventors identified targets within the genome for amplification. Oligonucleotide RT-PCR primers were designed that amplify genomic SARS-CoV RNA (gRNA) or the sgRNA that is specific to the leader-body junction. Because genomic RNA is present in input virus, the inventors probed for sgRNA, which is indicative of virus entry and/or replication Genomic RNA was detected by amplifying a region between the 1b coding region of the polymerase gene and the sequence encoding the Spike (S) glycoprotein. Subgenomic RNA was detected using a primer specific to the leader sequence in conjunction with the reverse primer in S that was used for the gRNA detection. G3PDH primers, designed to amplify G3PDH from multiple species, served as a positive control for RNA integrity and cDNA production.

To evaluate the RT-PCR assay, Vero E6 cells were inoculated with serial dilutions of SARS-CoV ranging from an MOI of $10^0$ to $10^{-8}$ $TCID_{50}$/cell. Total RNA was extracted at 1 and 24 h post-inoculation (p.i.). At 1 hr p.i. gRNA was detected in cells inoculated with virus at an MOI of $10^0$ to $10^{-2}$, as indicated by a band at 300 bp (FIG. 1). Subgenomic RNA was not detected (180 bp). However, at 24 hr p.i. both gRNA and sgRNA, 300 bp and 180 bp respectively, were detected in cells inoculated with an MOI of $10^0$ to $10^{-5}$. The sgRNA amplicon was confirmed to correspond to the S leader-body junction sgRNA by sequence analysis (Thiel, et al., 2003, J. Gen. Virol. 84:2305-2315). Genomic RNA was visible at 24 hr p.i. in cells inoculated with an MOI of $10^{-7}$, however this was not seen, in repeated experiments. The decrease in amplified G3PDH (~800 bp), as seen in lanes 1-6 at 24 hr p.i., was consistent between repeated experiments. The decrease in G3PDH may be a result of the RT-PCR conditions, which were optimized to favor amplification of SARS-CoV gRNA and sgRNA. Individual amplicon were amplified by PCR of cDNAs from the same samples and G3PDH was consistently detected. Additionally, the decrease in G3PDH may be due to cell death, which is seen in Vero E6 cells. G3PDH was included as a control for template concentration and RNA integrity, and was always detected in the absence of viral RNA.

This data demonstrates that the exemplary multiplex RT-PCR assays is sensitive for detection of SARS-CoV infection.

Example 12

Cytophathic Effect does not Always Correlate with SARS-CoV Infection

This example shows replication of SARS-CoV, as detected by sgRNA and virus titers, in the absence of CPE. In particulare, significant CPE was not observed in pRhMK, pCMK, R-mix (Mv1Lu and A549), Mv1Lu, HEK-293T, and Huh-7 cells at 5 days post infection, although virus titers as well as SARS-CoV sgRNA were actually increased within 24 hours post infection (Table 12).

TABLE 12

Susceptibility Of Cells To Sars-Coronavirus

| Cell | Species of Origin | SARS-CoV sgRNA | CPE | Titer[a] |
|---|---|---|---|---|
| VeroE6 | African green monkey | + | + | $2.4\times10^7$ |
| pRhMK | Rhesus macaque | + | − | $5.6\times10^5$ |
| PCMK | Cynomolgous macaque | + | − | $7.8\times10^4$ |
| R-Mix | Mink and Human | + | − | $7.8\times10^3$ |
| A549 | Human | − | − | <1[b] |
| Mv1Lu | Mink | + | − | $2.5\times10^4$ |
| HEL | Human | − | − | <1 |
| MRC-5 | Human | − | − | <1 |
| MDCK | Canine | − | − | <1 |
| AK-D | Feline | − | − | ND[c] |
| L2 | Murine | − | − | ND |
| HRT-18 | Human | | − | ND |
| CEF | Chicken | − | − | ND |
| HEK-293T | Human | + | − | $5.6\times10^3$ |
| Huh-7 | Human | + | − | $1.3\times10^5$ |
| CMT-93 | Murine | − | − | ND |
| CMT-93/hAPN | Murine | − | − | ND |
| BHK-21 | Syrian hamster | − | − | <1 |
| BHK-21/hAPN | Syrian hamster | − | − | ND |

[a]Titer = $TCID_{50}$/ml at 48 hr post-inoculation.
[b]Below the limit of detection
[c]Titer not determined.

Example 13

Testing Influenza Virus Susceptibility of Human Lung Cell Lines

Although primary monkey kidney cells are the gold standard for influenza isolation, there are many drawbacks to their use, such as indigenous viruses; and long quarantine periods. The mixed cell systems described herein has been developed to isolate all of the viruses that infect primary monkey kidney cells (pRHMK), such as respiratory viruses, herpes viruses and enteric viruses, while overcoming the problems typically associated with primary monkey kidney cells. This example describes the selection of a continuous human lung cell suitable for use in the mixed cell cultures of the present invention.

Briefly, seven human lung epithelial cells were purchased from ATCC: HTB-53 (A-427), HTB-54 (Calu-1), HTB-55 (Calu-3), HTB-56 (Calu-6), HTB-57 (SK-LU-1), HTB-58 (SK-MES-1), and HTB-59 (SW 900). These cells were cultured in 24 well cluster plates in plating medium supplemented with 10% FBS, and 1% Pen-Strep solution. When monolayers of each cell line became confluent, the plating medium was removed, and replaced with RM03 medium without serum. The cells were then inoculated with several different strains of influenza A virus: (A/Port Chalmers (H3N2), A/Victoria (H3N2), A/PR(H1N1), A/Malaysia (H1N1); and several different strains of influenza B virus: (B/Massachusetts, B/Maryland, B/Taiwan and B/Hong Kong). The target input for each virus was an MOI of 0.001. The infected cells were placed in a humidified 35-37° C., 5% $CO_2$ incubator. A sample of medium was removed from each monolayer on a daily basis for 6 days, and assayed for hemagglutination, (HA). The HA assay was performed by diluting the original sample 1:8 with phosphate buffer saline (PBS), followed by 2 fold dilutions in PBS until a 1:256 dilution was reached. An equal volume of washed 1% guinea pig red blood cells (RBC) were added to each tube, mixed gently and then incubated at room temperature for 1 hr. The monolayers were recorded as positive when the RBC were forming a circular sheet at the bottom of the round-bottom tube and negatives showed a drop of RBC at the very bottom of the tube. The highest titers showing evidence of infection are shown in Tables 13 and 14. On day 6, 200 µl of washed 1% RBC was added to the each of the cell monolayers and incubated at room temperature for 1 hr for hemadsorption, (HAD). The cell monolayers were shaken gently to disassociate the loose RBC that did not adsorb onto the monolayer. The contents were then gently poured out for observation under the inverted microscope. Positive monolayers had clumps of RBC tightly adsorbed to them, while negative monolayers did not.

that 50% of the monolayer adsorbed RBC, "+++" indicates that 75% of the monolayer adsorbed RBC, and "++++" indicates that nearly 100% of monolayer adsorbed RBC. Surprisingly, Calu-3 appears to be a unique in its permissivity of influenza A and B virus replication. In contrast, the other human lung epithelial cell lines tested performed poorly or did not support any measurable influenza A and/or B virus replication.

Example 14

Mixed Cell Cultures Comprising Calu-3 Cells for Detection and Amplification of Respiratory Viruses As described in Example 13 above, Calu-3 cells are a continuous human lung adenocarcinoma epithelial cell line that was chosen from a panel of 7 human lung cell lines for its ability to detect and amplify both influenza A and influenza B virus. A549 cells are continuous human lung carcinoma cells that have been shown to be suitable for isolation of adenoviruses, herpes viruses and enteric viruses. The A549 cell line is used in the R-Mix, R-Mix Too and Super E-Mix Mixed Culture Systems available for Diagnostic Hybrids (Athens, Ohio).

Mixed cell cultures were produced by co-plating the Calu-3 and A549 individual cell cultures at a ratio of 6.5:1 in shell vials with coverslips and in 16 mm glass round tubes. The mixture of these two cell lines produced an evenly distributed monolayer with two distinct morpholo-

TABLE 13

Infection of Human Lung Epithelial Cells With Influenza A Viruses

| Cell Line | A/Port (H3N2) | | A/Vic (H3N2) | | A/PR (H1N1) | | A/Mala (H1N1) | |
|---|---|---|---|---|---|---|---|---|
| | HA | HAD | HA | HAD | HA | HAD | HA | HAD |
| Calu-3 | 1:256 | ++++ | 1:256 | ++++ | 1:256 | ++++ | 1:256 | ++++ |
| SK-LU-1 | <1:8 | − | <1:8 | − | <1:8 | − | <1:8 | − |
| Calu-1 | <1:8 | + | <1:8 | − | <1:8 | − | <1:8 | + |
| Calu-6 | <1:8 | − | <1:8 | − | <1:8 | − | <1:8 | − |
| SW 900 | <1:8 | − | <1:8 | − | <1:8 | − | <1:8 | − |
| SK-MES-1 | <1:8 | − | <1:8 | − | <1:8 | − | <1:8 | − |
| A-427 | <1:8 | − | <1:8 | − | <1:8 | − | <1:8 | − |

TABLE 14

Infection of Human Lung Epithelial Cells With Influenza B Viruses

| Cell Line | B/Mass | | B/MD | | B/Tai | | B/HK | |
|---|---|---|---|---|---|---|---|---|
| | HA | HAD | HA | HAD | HA | HAD | HA | HAD |
| Calu-3 | 1:64 | ++++ | 1:64 | ++++ | 1:32 | ++ | 1:32 | ++ |
| SK-LU-1 | <1:8 | − | <1:8 | ++ | <1:8 | − | <1:8 | − |
| Calu-1 | <1:8 | − | <1:8 | + | <1:8 | + | <1:8 | + |
| Calu-6 | <1:8 | − | <1:8 | − | <1:8 | − | <1:8 | − |
| SW 900 | <1:8 | − | <1:8 | + | <1:8 | − | <1:8 | − |
| SK-MES-1 | <1:8 | − | <1:8 | + | <1:8 | − | <1:8 | − |
| A-427 | <1:8 | − | <1:8 | − | <1:8 | − | <1:8 | − |

The numbers in Tables 13 and 14 refer to the dilution that was HA positive, with <1:8 indicating that the culture was negative at the initial 1:8 dilution. These results demonstrate that only Calu-3 cells were able to support replication of influenza A and B viruses for production of high virus yields. The HAD results are as follows: "+" indicates that approximately 25% of the monolayer adsorbed RBC, "++" indicates gies at points of confluency. Confluent T-225 flasks of Calu-3 cells were prepared in Opti-Mem Medium, with 10% FBS, 4 mM L-glutamine and 1% Pen-Strep solution. Confluent T-225 flasks of A549 cells were prepared in EMEM with HEPES, 10% FBS, 2 mM L-glutamine and 50 µg/ml gentamicin. Both cell lines were harvested by first rinsing them in 30 ml HESS without magnesium and calcium. The cells were then dissociated from the flasks by exposure to 7 ml trypsin-EDTA solution. A549 cells require only 5-10 minutes of contact with the trypsin solution at room temperature to become detached, while Calu-3 cells require 20-30 minutes of contact with the trypsin solution at 37° C. to become detached. About 23 mls of the cells respective culture media, was added to each flask after the cells were visibly detached from the plastic. The cell suspensions were then pipetted several times to form a homogenous suspension. Following a standard procedure for counting cells using a hemocytometer, the concentration in cells/ml for each cell line was determined. Based on their concentrations, about 100,000 Calu-3 cells and 15,000 A549 cells were added to 50 mls of Opti-Mem medium, supplemented with 4% FBS, 4 mM L-glutamine and 1% pen-strep solution. This ratio gives an approximate 60%:40% ratio of Calu-3:A549 cells when the monolayer reaches confluency after 6-7 days incubation when plated in shell vials with coverslips at 1 ml/vial. For 16 mm glass round tubes, the same plate density was used, except the tubes were seeded with 2 mls/tube instead of 1 ml. This also gave a confluent monolayer in 6-7 days. Neither culture format required 5% $CO_2$ or 95% humidity since they are both closed, air-tight systems. However, if multiwell cluster plate formats are used, the cultures are incubated in a humidified, 5% $CO_2$ incubator. Monolayers of Calu-3/A549 and pRHMK cells in shell vials with coverslips, (from DHI), were refed with 1 ml of RM03, (Opti-Mem with Pen-Strep solution), without serum. The frozen original clinical specimens (these specimens were determined to be positive by antigen assay with fluorescent antibody staining) in M4 transport medium were inoculated onto both cell monolayers. Shell vials were centrifuged at 700×g for 1 hr and then incubated at 35° C. for 3 days. The monolayers infected with Influenza A and B, and Parainfluenza 1, 2 and 3 were tested for hemadsorption, (HAD), by adding Guinea pig RBC to those vials and incubating them at 4° C. for 30 minutes to allow the red blood cells to "stick" to the infected cells. After HAD for each monolayer was assessed, the RBC were removed and cell monolayers fixed with 80% acetone and stained with DHI $D^3$ monoclonal antibodies specific for the virus that was inoculated into each monolayer.

As shown in Table 15, the Calu-3/A549 mixed cell cultures detected one more low positive Flu A sample and showed more positive HAD and positive stained cells than pRHMK cells. The results are comparable for the 3 high positive Flu B samples. Only one sample of Parainfluenza 2 was detected by both cell monolayers and both cells have similar levels of positively stained cells. All three samples of Parainfluenza 3 were detected by both cell monolayers but pRHMK cells showed a slightly higher level of positively stained cells, Calu-3/A549 cells detected all three positive adenovirus samples while pRHMK cells only detected two positives indicating that the mixed cells might be more sensitive than the pRHMK cells for adenovirus detection. Calu-3/A549 cells detected two out of three RSV samples, although the number of positively stained cells was low. In contrast, none of the three RSV viruses could be detected with the pRHMK cells. Thus, Calu-3/A549 cells are comparable or more sensitive than pRHMK cells for detection of all respiratory viruses tested, with the exception of Parainfluenza 3 virus.

TABLE 15

Comparison of Calu-3/A549 Mixed Cell Cultures and pRHMK Cells For Respiratory Virus Detection

| Virus | | Calu-3/A549 | | pRHMK | |
|---|---|---|---|---|---|
| Sample | | HAD | FA stain | HAD | FA stain |
| Flu A | 1 | + | 244 | − | − |
|  | 2 | + | 2+ | + | + |
|  | 3 | 3+ | 3+ | + | + |
| Flu B | 1 | 2+ | 4+ | 2+ | 4+ |
|  | 2 | 3+ | 4+ | 3+ | 4+ |
|  | 3 | 3+ | 4+ | 3+ | 4+ |
| Para2 | 1 | + | 4+ | + | 4+ |
|  | 2 | − | − | − | − |
|  | 3 | − | − | − | − |
| Para3 | 1 | + | 3+ | + | 4+ |
|  | 2 | + | 2+ | + | 4+ |
|  | 3 | + | 3+ | + | 4+ |
| Adeno | 1 | n/a | 4+ | n/a | 3+ |
|  | 2 | n/a | 3+ | n/a | 2+ |
|  | 3 | n/a | 4+ | n/a | − |
| RSV | 1 | n/a | + | n/a | − |
|  | 2 | n/a | 7 | n/a | − |
|  | 3 | n/a | − | n/a | − |

Calu-3 shell vials with coverslips and MDCK shell vials with coverslips were refed with (1 ml/vial of RM03). Multiple strains of influenza A virus (A/Vict, A/Aichi, A/Port, A/Denver, A/HK, A/PR, A/WS, and A/Mala,) and influenza B virus (B/Mass, B/MD and B/Tai) were inoculated at an MOI of 0.001 in the designated shell vials of each cell line and centrifuged for 1 hr at 700×g. A sample of supernatant was collected daily from each vial and inoculated into a corresponding Mink Lung shell vial. The Mink Lung vials were then centrifuged for 1 hr at 700×g, then incubated overnight (~16-18 hours), at 35° C. Monolayers were then fixed with 80% acetone and stained with the appropriate DHI $D^3$ Flu A or B monoclonal antibody. Virus yield from the Calu-3 and MDCK cells was determined by the number of positive fluorescence cells in each of the Mink Lung cultures.

The highest titers reached are shown in Table 16. For most of the viruses tested, Calu-3 cells produced more virus (higher yield) than the MDCK cells, with the exception of Influenza B/Taiw in which Calu-3 cells yielded a 3 to 4 fold lower titer than the MDCK cells. These results indicate that Calu-3 cells are a superior cell line for influenza virus amplification.

TABLE 16

Comparison Of Calu-3 And MDCK Cells For Influenza A and B Virus Amplification

| virus strain | MDCK | Calu-3 |
|---|---|---|
| B/Mass | $7 \times 10^8$ | $9 \times 10^8$ |
| B/MD | $1 \times 10^8$ | $1.8 \times 10^8$ |
| B/Tai | $2 \times 10^8$ | $6 \times 10^7$ |
| A/Vict (H3N2) | $1.3 \times 10^8$ | $9 \times 10^8$ |
| A/Port (H3N2) | $1.1 \times 10^8$ | $2.7 \times 10^9$ |
| A/Aichi (H3N2) | $7.8 \times 10^6$ | $5 \times 10^8$ |
| A/Den (H3N2) | $9 \times 10^7$ | $1.6 \times 10^8$ |
| A/HK (H3N2) | $1.2 \times 10^6$ | $4.8 \times 10^8$ |
| A/PR (H1N1) | $2 \times 10^8$ | $2 \times 10^9$ |
| A/WS (H1N1) | $9.7 \times 10^8$ | $1.4 \times 10^9$ |
| A/Mala (H1N1) | $3 \times 10^8$ | $9.9 \times 10^9$ |

Example 15

Mixed Cell Cultures Comprising Calu-3 Cells for Detection and Amplification of Herpes Viruses Using the ELVIS HSV detection system from Diagnostic Hybrids, the supernatant from infected Calu-3/A549 and pRHMK 16 mm glass round tube cultures was tested at 24, 48 and 72 hours post inoculation. At each time point, 200 µl of supernatant was removed from duplicate tubes and centrifuged onto ELVIS shell vials with coverslips. ELVIS cultures were incubated for 18 hrs before processing using ELVIS Solutions 1 and 2 as directed by the manufacturer.

Results shown in Table 17 are as follows: single numbers represent individual infected (blue stained) cells, while 1+=25%, 2+=50%, 3+=75% and 4+=100% represent percentages of ELVIS monolayer infected. Each value is an average of duplicate ELVIS shell vials. Thus, Calu-3/A549 mixed cells cultures are also suitable for detection and amplification of HSV types 1 and 2. Moreover, the Calu-3/A549 mixed cell cultures more rapidly amplified HSV, and yielded a higher HSV titer than did the pRHMK cultures.

TABLE 17

Comparison of Calu-3/A549 Mixed Cell Cultures and pRHMK Cells For HSV Detection And/Or Amplification

| virus | Calu-3/A549 mix | pRHMK |
|---|---|---|
| HSV-1 Day 1 | 233 | 35 |
| HSV-1 Day 2 | 4+ | 4+ |
| HSV-1 Day 3 | 4+ | 4+ |
| HSV-2 Day 1 | 7 | 0.5 |
| HSV-2 Day 2 | 1+ | 350 |
| HSV-2 Day 3 | 2+ | 1+ |

Example 16

Mixed Cell Cultures Comprising Calu-3 Cells for Detection and Amplification of Enteric Viruses Monolayers of Calu-3/A549 mixed cell cultures and pRHMK cells in 24-well plates were refed with MEM containing 0.1% FBS. The frozen enterovirus prototypes obtained from ATCC (virus titer was undetermined) were arbitrarily diluted 1:1000 in medium and inoculated onto both monolayers. Culture plates were incubated at 35° C. for 3 days and the development of cytopathic effect (CPE) was observed and recorded daily.

In Table 18, B1 to B6 refer to Coxsackie B viruses, 68 to 71 refer to enteroviruses, and E1 to E29 refer to echoviruses. Results are shown as follows: – indicates no CPE, + indicates 25%, ++ indicates 50%, +++ indicates 75% and ++++ indicates 100% CPE. As described herein, the Calu-3/A549 mixed cell cultures are able to support replication of most enteroviruses as well if not better than pRHMK cells, although enterovirus 71 was not detected by either cell preparation (indicative of very low or no live virus in the sample). Of the viruses tested, B4, 70 and E2 were detected later in Calu-3/A549 mixed cells than in pRHMK cells, and enterovirus 69 and E21 were detected by Calu-3/A549 mixed cells but not pRHMK cells. Importantly, on day 1 the mixed cells detected more viruses than did the pRhMK cells, indicating that the Calu-3/A549 mixed cells are more sensitive for early detection, which is important for diagnosis of patient samples, Likewise, the Calu-3/A549 mixed cells showed more extensive CPE than the pRHMK cells in most of the virus samples. Thus, the Calu-3/A549 mixed cell cultures described herein are able to support the propagation of a wide variety of enteroviruses, clearly demonstrating that these mixed cells are suitable for use in clinical diagnostic applications.

TABLE 18

Comparison of Calu-3/A549 Mixed Cell Cultures and pRHMK Cells For Enteric Virus Detection

| Sample | RhMK | | | Calu-3/A549 | | |
|---|---|---|---|---|---|---|
| (virus) | Day 1 | Day 2 | Day 3 | Day 1 | Day 2 | Day 3 |
| B1 | – | + | ++ | + | ++++ | ++++ |
| B2 | + | + | ++ | + | ++++ | ++++ |
| B3 | + | ++ | ++ | + | ++++ | ++++ |
| B4 | – | + | + | – | – | + |
| B6 | – | + | + | + | ++ | ++++ |
| 68 | – | – | + | – | – | + |
| 69 | – | – | – | – | ++ | +++ |
| 70 | – | + | ++ | – | – | + |
| 71 | – | – | – | – | – | – |
| E1 | – | + | +++ | + | +++ | ++++ |
| E2 | – | + | + | – | – | + |
| E3 | – | + | + | – | + | +++ |
| E6 | – | ++ | ++ | – | ++ | ++++ |
| E7 | – | + | + | + | ++++ | ++++ |
| E8 | – | – | + | – | ++ | ++++ |
| E9 | – | + | + | – | + | + |
| E11 | – | + | + | + | +++ | ++++ |
| E12 | – | + | +++ | – | + | ++ |
| E13 | – | + | + | – | ++ | ++++ |
| E19 | – | + | ++ | + | +++ | ++++ |
| E21 | – | – | – | – | + | ++++ |
| E24 | – | + | + | – | ++ | ++++ |
| E25 | – | + | + | – | + | ++++ |
| E29 | – | + | ++ | – | + | ++ |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostic microbiology and virology, cell culture, and/or related fields are intended to be within the scope of the following claims. From the above, it is clear that the present invention provides many advantages over presently used methods in diagnostic microbiology.

The invention claimed is:

1. A composition comprising cells suitable for the detection of a respiratory virus, wherein the cells comprise mink lung cells, H292 cells and A549 cells.

2. The composition according to claim 1, wherein the mink lung cells are Mv1Lu cells.

3. The composition of claim 1, wherein the composition is suitable for detection of a parainfluenza virus, respiratory syncytial virus (RSV), adenovirus, influenza viruses, and cytomegalovirus (CMV).

4. The composition of claim 1, wherein the composition is suitable for detection of a herpes virus.

* * * * *

SEQUENCE LISTING

<160> NUMBER OF SEQ ID NOS: 11

<210> SEQ ID NO 1
<211> LENGTH: 72
<212> TYPE: DNA
<213> ORGANISM: SARS coronavirus

<400> SEQUENCE: 1
atattaggtt tttacctacc caggaaaagc caaccaacct cgatctcttg tagatctgtt    60
ctctaaacga ac    72

<210> SEQ ID NO 2
<211> LENGTH: 71
<212> TYPE: DNA
<213> ORGANISM: SARS coronavirus

<400> SEQUENCE: 2
tattaggttt ttacctaccc aggaaaagcc aaccaacctc gatctcttgt agatctgttc    60
tctaaacgaa c    71

<210> SEQ ID NO 3
<211> LENGTH: 68
<212> TYPE: DNA
<213> ORGANISM: SARS coronavirus

<400> SEQUENCE: 3
taggttttta cctacccagg aaaagccaac caacctcgat ctcttgtaga tctgttctct    60
aaacgaac    68

<210> SEQ ID NO 4
<211> LENGTH: 57
<212> TYPE: DNA
<213> ORGANISM: SARS coronavirus

<400> SEQUENCE: 4
ctacccagga aaagccaacc aacctcgatc tcttgtagat ctgttctcta aacgaac    57

<210> SEQ ID NO 5
<211> LENGTH: 56
<212> TYPE: DNA
<213> ORGANISM: SARS coronavirus

<400> SEQUENCE: 5
tacccaggaa aagccaacca acctcgatct cttgtagatc tgttctctaa acgaac    56

<210> SEQ ID NO 6
<211> LENGTH: 53
<212> TYPE: DNA
<213> ORGANISM: SARS coronavirus

<400> SEQUENCE: 6
ccaggaaaag ccaaccaacc tcgatctctt gtagatctgt tctctaaacg aac    53

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
catcaccatc ttccaggagc    20

<210> SEQ ID NO 8
<211> LENGTH: 20
<212> TYPE: DNA
<213> ORGANISM: Artificial Sequence
<220> FEATURE:

```
<223> OTHER INFORMATION: Synthetic

<400> SEQUENCE: 8
cttactcctt ggaggccatg                                            20

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
tgctaactac attttctgga gg                                         22

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
agtatgttga gtgtaattag gag                                        23

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
atattaggtt tttacctacc cagg                                       24
```